US008563248B2

(12) United States Patent
Smith et al.

(10) Patent No.: US 8,563,248 B2
(45) Date of Patent: Oct. 22, 2013

(54) COMPOSITIONS AND METHODS FOR DETECTION OF COLORECTAL CANCER

(76) Inventors: Jeffrey W. Smith, La Jolla, CA (US); Changming Fang, La Jolla, CA (US)

(*) Notice: Subject to any disclaimer, the term of this patent is extended or adjusted under 35 U.S.C. 154(b) by 0 days.

(21) Appl. No.: 12/959,349

(22) Filed: Dec. 2, 2010

(65) Prior Publication Data

US 2011/0200996 A1    Aug. 18, 2011

Related U.S. Application Data

(63) Continuation of application No. 11/992,279, filed as application No. PCT/US2006/037103 on Sep. 21, 2006, now abandoned.

(60) Provisional application No. 60/719,747, filed on Sep. 21, 2005.

(51) Int. Cl.
*C07H 21/04* (2006.01)
*C12Q 1/68* (2006.01)

(52) U.S. Cl.
USPC .................. 435/6.11; 435/6.12; 435/91.2

(58) Field of Classification Search
None
See application file for complete search history.

(56) References Cited

PUBLICATIONS

Enard et al (Science. 2002. Apr. 12; 296(5566):340-43).*
Hoshikawa et al Physiol Genomics (2003) 12:209-219.*
Chan, Drug Discovery and Development, Apr. 2006, vol. 6 No. 3, 1-6.*
Cheung, Cold Spring Harbor Symposia Quant Biol, vol. 68, pp. 403-407.*
Michiels et al. Lancet, 2005; 365:488-492.*
Slonim, Nature Genetics Supplement, vol. 32, Dec. 2002, pp. 502-508.*
Baker. Journal of the National Cancer Institute, vol. 95, No. 7, Apr. 2, 2003, 511-515.*
Pusztai and Hess, Annals of Oncology, vol. 15, pp. 1731-1737, 2004.*
Golub et al (Science, vol. 286, pp. 531-537, Oct. 1999.*
de Gottardi (Dig Diseases and Sciences, 2004, vol. 49, pp. 982-989).*
Cheung, Cold Spring Harbor Symposia Quant Biol, 2003, vol. 68, pp. 403-407.*

* cited by examiner

*Primary Examiner* — Sarae Bausch

(57) ABSTRACT

We have identified a new variant of ileal bile acid binding protein (IBABP), designated IBABP-L, which is a biomarker for colorectal cancer. The transcript for IBABP-L arises from an alternative start site and includes three exons that are absent in IBABP. IBABP-L also shares part of a fourth exon with IBABP. The protein encoded by IBABP-L contains a deduced 49 residue N-terminal sequence that is not found in the IBABP protein. The present invention provides methods for diagnosing colorectal cancer and other compositions and methods based on this discovery.

4 Claims, 8 Drawing Sheets

Fig. 1

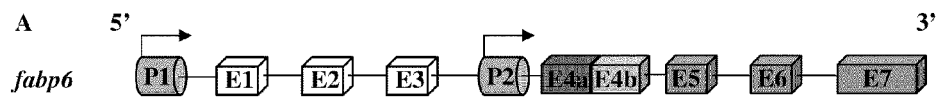

Fig. 2

```
GGCGACAACAAAACAGATTACTTTGAAGGGACTAGAAGGAGGACACAGGGTCCTGGAGGAAGGC
AGCTGGCAAGTTACAGAGCAGAAAGACTTTGCACCTCTGGCTCCAGGGAGCTCACAGGCAGGGG
CTGGTCCAGCCCAGAGGCGATGAAGACAGTGACGATGATGATGGTGGTGGAGATGCAGGCGCTG
ACTCAGCTGTCTCTCTGTGACTGTCTTTGTGACAGTCTCATTGTTGTTGTTACTAAGATGGCTT
CCCTCAGAGGACGGACACTTGGAGTAGTGGCAGGTTCGGCCACCCCTAGAGACGATGGCGGTGG
GGACCGGGGCAGCCCCCTGGCCCCCTGGGCTCACCCCCGTCCTGCGCCACCCCGGGCCGTGCCG
TGCCAAGCCGGCCACCAGAGGGCGCGCCAGGTCGCGGCATCCCGGCTCCCCGTCGGCCTGGGGC
CGGCGGGCGGGGCTCGGCTGTCTCCTACTGAGGCCTCGCACTTCCTCTCTTGTACTTCTGTGTT
TCTTGGAGAGCTGCTCCTTGAAGATACTGCTGCATGTGGGTGTCTGTGGGACTGTCAGTTAAGA
GCCTCCACTGGCCTCACCCACCCCCAGAGGGAATACATGTCCTCGGCTGAGCCCATTGGGCTTT
CTCTCCTGACCAATCAGATTATTTCTCTTCTGACTCAGGTTCTGAGAGCTGTGTTGTCTGCGTG
CACATGGGTGAGCCGGAAAGGAGACCTGCAGAGAATGAAACAGACACATAAAGGAAAGCCTCCC
AGCAGCATGGCTTTCACCGGCAAGTTCGAGATGGAGAGTGAGAAGAATTATGATGAGTTCATGA
AGCTCCTTGGGATCTCCAGCGATGTAATCGAAAAGGCCCGCAACTTCAAGATCGTCACGGAGGT
GCAGCAGGATGGGCAGGACTTCACTTGGTCCCAGCACTACTCCGGGGGCCACACCATGACCAAC
AAGTTCACTGTTGGCAAGGAAAGCAACATACAGACAATGGGGGGCAAGACGTTCAAGGCCACTG
TGCAGATGGAGGGCGGGAAGCTGGTGGTGAATTTCCCCAACTATCACCAGACCTCAGAGATCGT
GGGTGACAAGCTGGTGGAGGTCTCCACCATCGGAGGCGTGACCTATGAGCGCGTGAGCAAGAGA
CTGGCCTAAGCAGCCAGGCCCGGCCCAGGGAGCTACAAACCCACCAATAAAACTGATATAAGGA
CAAAAAAAAAAAAAAAAA  (SEQ ID NO: 1)
```

Fig. 3

ATGAAGACAGTGACGATGATGATGGTGGTGGAGATGCAGGCGCTGACTCAGCTGTCTCTCTGTG
ACTGTCTTTGTGACAGTCTCATTGTTGTTGTTACTAAGATGGCTTCCCTCAGAGGACGGACACT
TGGAGTAGTGGCAGGTTCGGCCACCCCTAGAGACGATGGCGGTGGGGACCGGGGCAGCCCCCTG
GCCCCCTGGGCTCACCCCCCTCCTGCGCCACCCCGGGCCGTGCCGTGCCAAGCCGGCCACCAGA
GGGCGCGCCAGGTCGCGGCATCCCGGCTCCCCGTCGGCCTGGGGCCGGCGGGCGGGGCTCGGCT
GTCTCCTACTGAGGCCTCGCACTTCCTCTCTTGTACTTCTGTGTTTCTTGGAGAGCTGCTCCTT
GAAGATACTGCTGCATGTGGGTCTCTGTGGGACTGTCAGTTAAGAGCCTCCACTGGCCTCACCC
ACCCCAGAGGGAATACATGTCCTCGGCTGAGCCCATTGGGCTTTCTCTCCTGACCAATCAGAT
TATTTCTCTTCTGACTCAGGTTCTGAGAGCTGTGTTGTCTGCGTGCACATGGGTGAGCCGGAAA
GGAGACCTGCAGAGAATGAAACAGACACATAAAGGAAAGCCTCCCAGCAGC  (SEQ ID NO: 2)

*Fig. 4*

CAGCGACAACAAAACAGATTACTTTGAAGGGACTAGAAGGAGGACACAGGG
TCCTGGAGGAAGGCAGCTGGCAAGTTACAGAGCAGAAAGACTTTGCACCTCT
GGCTCCAGGGAGCTCACAGGCAGGGGCTGGTCCAGCCCAGAGGCGATGAAG
ACAGTGACGATGATGATGGTGGTGGAGATGCAGGCGCTGACTCAGGTTCTGA
GAGCTGTGTTGTCTGCGTGCACATGGGTGAGCCGGAAAGGAGACCTGCAGAG
AATGAAACAGACACATAAAGGAAAG-------------------------------------------
------------------------------------GAAGAAGTGGGGTGACTTAGGGGCT
GAGCCTCAGCAACTGGGAGAGTTTATAAGCTGGATAGCAGACCCCTCAGCAC
----------------------------------------------------------------CCTCCCAGCAGCATG
CACCCATTCTCCTCATCCCTCTGCTCTCTGGCCTCCAGCCTCCCAGCAGCATG
GCTTTCACCGGCAAGTTCGAGATGGAGAGTGAGAAGAATTATGATGAGTTCA
GCTTTCACCGGCAAGTTCGAGATGGAGAGTGAGAAGAATTATGATGAGTTCA
TGAAGCTCCTTGGGGATCTCCAGCGATGTAATCGAAAAGGCCCGCAACTTC
TGAAGCTCCTTGGGGATCTCCAGCGATGTAATCGAAAAGGCCCGCAACTTC
AAGATCGTCACGGAGGTGCAGCAGGATGGGCAGGACTTCACTTGGTCCCAG
AAGATCGTCACGGAGGTGCAGCAGGATGGGCAGGACTTCACTTGGTCCCAG
CACTACTCCGGGGGCCACACCATGACCAACAAGTTCACTGTTGGCAAGGAA
CACTACTCCGGGGGCCACACCATGACCAACAAGTTCACTGTTGGCAAGGAA
AGCAACATACAGACAATGGGGGGCAAGACGTTCAAGGCCACTGTGCAGATG
AGCAACATACAGACAATGGGGGGCAAGACGTTCAAGGCCACTGTGCAGATG
GAGGGCGGGAAGCTGGTGGTGAATTTCCCCAACTATCACCAGACCTCAGAG
GAGGGCGGGAAGCTGGTGGTGAATTTCCCCAACTATCACCAGACCTCAGAG
ATCGTGGGTGACAAGCTGGTGGAGGTCTCCACCATCGGAGGCGTGACCTATG
ATCGTGGGTGACAAGCTGGTGGAGGTCTCCACCATCGGAGGCGTGACCTATG
AGCGCGTGAGCAAGAGACTGGCCTAAGCAGCCAGGCCCGGCCCAGGGAGCT
AGCGCGTGAGCAAGAGACTGGCCTAAGCAGCCAGGCCCGGCCCAGGGAGCT
ACAAACCCACCAATAAAACTGATATAAGGAC  (SEQ ID NO: 3)
ACAAACCCACCAATAAAACTGATATAAGGAC  (SEQ ID NO: 4)

Fig. 5

```
ATGAAGACAGTGACGATGATGATGGTGGTGGAGATGCAGGCGCTGACTCAGGTTCTGAGAGCTG
TGTTGTCTGCGTGCACATGGGTGAGCCGGAAAGGAGACCTGCAGAGAATGAAACAGACACATAA
AGGAAAGCCTCCCAGCAGCATGGCTTTCACCGGCAAGTTCGAGATGGAGAGTGAGAAGAATTAT
GATGAGTTCATGAAGCTCCTTGGGATCTCCAGCGATGTAATCGAAAAGGCCCGCAACTTCAAGA
TCGTCACGGAGGTGCAGCAGGATGGGCAGGACTTCACTTGGTCCCAGCACTACTCCGGGGGCCA
CACCATGACCAACAAGTTCACTGTTGGCAAGGAAAGCAACATACAGACAATGGGGGGCAAGACG
TTCAAGGCCACTGTGCAGATGGAGGGCGGGAAGCTGGTGGTGAATTTCCCCAACTATCACCAGA
CCTCAGAGATCGTGGGTGACAAGCTGGTGGAGGTCTCCACCATCGGAGGCGTGACCTATGAGCG
CGTGAGCAAGAGACTGGCCTAAGCAGCCAGGCCCGGCCCAGGGAGCTACAAACCCACCAATAAA
ACTGATATAAGGACAAAAAAAAAAAAAAAAA  (SEQ ID NO: 5)
```

Fig. 6

```
ATGAAGACAGTGACGATGATGATGGTGGTGGAGATGCAGGCGCTGACTCAGGTTCTGAGAGCTG
TGTTGTCTGCGTGCACATGGGTGAGCCGGAAAGGAGACCTGCAGAGAATGAAACAGACACATAA
AGGAAAGCCTCCCAGCAGC  (SEQ ID NO: 6)
```

*Fig. 7*

MKTVMMMVVEMQALTQVLRAVLSACTWVSRKGDLQRMKQTHKGKPPSS

MAFTGKFEMESEKNYDEFMKLLGISSDVIEKARNFKIVTEVQQDGQDFTWSQHY
MAFTGKFEMESEKNYDEFMKLLGISSDVIEKARNFKIVTEVQQDGQDFTWSQHY

SGGHTMTNKFTVGKESNIQTMGGKTFKATVQMEGGKLVVNFPNYHQTSEIVGD
SGGHTMTNKFTVGKESNIQTMGGKTFKATVQMEGGKLVVNFPNYHQTSEIVGD

KLVEVSTIGGVTYERVSKRLA (SEQ ID NO: 7)
KLVEVSTIGGVTYERVSKRLA (SEQ ID NO: 8)

MKTVTMMMVVEMQALTQVLRAVLSACTWVSRKGDLQRMKQTHKGKPPSSMAFTGKFEMESEKNY
DEFMKLLGISSDVIEKARNFKIVTEVQQDGQDFTWSQHYSGGHTMTNKFTVGKESNIQTMGGKT
FKATVQMEGGKLVVNFPNYHQTSEIVGDKLVEVSTIGGVTYERVSKRLA (SEQ ID NO: 9)

COMPOSITIONS AND METHODS FOR DETECTION OF COLORECTAL CANCER

CROSS-REFERENCE TO RELATED CASES

This application is a continuation of U.S. application Ser. No. 11/992,279, filed on Mar. 18, 2008, by Jeffrey W. Smith et al., and entitled "COMPOSITIONS AND METHODS FOR DETECTION OF COLORECTAL CANCER", which is a national phase patent application filed under 35 U.S.C. 371 of International Patent Application No. PCT/US2006/037103 filed Sep. 21, 2006, which claims the benefit of U.S. Provisional Application Ser. No. 60/719,747, filed Sep. 21, 2005, all of which are hereby incorporated by reference in their entirety.

STATEMENT OF GOVERNMENT RIGHTS

This invention was made with Government support under R21 CA 116329 awarded by the National Institutes of Health. The Government has certain rights in the invention.

BACKGROUND TECHNICAL FIELD

The present invention relates to the detection of colorectal cancer, particularly to biomarkers for colorectal cancer that are useful for diagnostic purposes.

BACKGROUND INFORMATION

Colorectal cancer is the third most prevalent malignancy in the United States with approximately 145,000 new diagnoses and 56,000 deaths estimated for 2005 [*Cancer Facts and Figures* 2005, Surveillance Research (Washington, D.C.: American Cancer Society, Inc.), 2005). The most common non-invasive test for colorectal cancer is the fecal occult blood test (FOBT), which has been used for more than thirty years. Unfortunately, the sensitivity of the FOBT remains around 50% and may not detect early malignancy since not all carcinomas shed blood (Agrawal and Syngal, Curr. Opin. Gastroenterol. 21:59-63, 2005). Because of the high number of false-positives associated with FOBT, colonoscopy and sigmoidoscopy remain the gold standard for detecting colon cancer (Smith et al., CA Cancer J. Clin. 55:31-44, 2005). These invasive exams are expensive, require highly trained staff, are uncomfortable, and raise the risk of bowel perforation and possible mortality (Davies et al., Nat. Rev. Cancer 5:199-209, 2005). Consequently, there is still a great need for new molecular markers of and diagnostic tests for colorectal cancer.

One might expect to find alterations in the expression of proteins associated with known risk factors for colon cancer, like bile acids, which were recognized as carcinogens as early as 1940 (Cook et al., Nature 145:627, 1940) and have since been strongly linked with the incidence of colon cancer (Wunder and Reddy, J. Natl. Cancer Inst. 50:1099-1106, 1973; Crowther et al., Br. J. Cancer 34:191-198, 1976; Reddy et al., Cancer 42:2832-2838, 1978; Jensen et al., Nutr. Cancer 4:5-19, 1982; Hill et al., Nutr. Cancer 4:67-73, 1982; Domellof et al., Nutr. Cancer 4:120-127, 1982). Only a few studies have examined proteins in the bile-acid response pathway as potential biomarkers in colorectal cancer (DeGottardi et al., Dig. Dis. Sci. 49:982-989, 2004).

One of the proteins involved in bile acid homeostasis is ileal bile acid binding protein (IBABP), a 14 kDa cytoplasmic protein that is part of the fatty acid binding protein (FABP) family. IBABP is encoded by the fabp6 gene on chromosome 5 (Fujita et al., Eur. J. Biochem. 233:406-423, 1995); IBABP is unique among this protein family because it binds to bile acids instead of fatty acids (Thompson et al., Mol. Cell. Biochem. 192:9-16, 1999). Moreover, bile acids induce the expression of IBABP (Kanda et al., Biochem. J. 330 (Pt. 1):261-265, 1998) by binding nuclear farnesoid-X receptor (FXR) in the intestine (Makishima et al., Science 284:1362-1365, 1999; Wang et al., Mol. Cell 3:543-553, 1999; Parks et al., Science 284:1365-1368, 1999), thereby activating a bile acid responsive element in the IBABP promoter (Grober et al., J. Biol. Chem. 274:29749-29754, 1999). Based on these properties, and its localization in intestinal epithelium, IBABP may be involved in bile acid transport and buffering activities central to control of cholesterol homeostasis (Fuchs, Am. J. Physiol. Gastrointest. Liver Physiol. 284: G551-G557, 2003).

There is a need for accurate and sensitive diagnostics to identify colorectal cancer in patients. The present invention meets this and other needs.

SUMMARY OF THE INVENTION

Our analysis of the gene structure of IBABP surprisingly reveals a new variant of IBABP that we call IBABP-L. IBABP-L arises from an alternative start site in the IBABP gene and consequently encodes a protein having a unique 49 amino acid-long sequence at its N-terminus. Most significantly, IBABP-L is up-regulated in all stages of colorectal cancer and in malignant colon polyps. By contrast, the expression of the shorter transcript encoding the 14 kDa IBABP is not significantly changed in colorectal cancer.

According to one embodiment of the invention, isolated polynucleotides are provided that comprise a sequence that has at least 90%, 95%, 99% or 100% nucleic acid sequence identity to a native IBABP-L polynucleotide and that hybridizes selectively to the native IBABP-L polypeptide.

According to another embodiment of the invention, isolated polynucleotides are provided that comprise a sequence at least 100 nucleotides in length that has at least 90%, or 95%, or 99% nucleic acid sequence identity to a native IBABP-L exon 1-3 polynucleotide, as defined below.

According to another embodiment of the invention, isolated polynucleotides are provided that comprise at least 15, 20, or 30 contiguous nucleotides of a native IBABP-L exon 1-3 polynucleotide, or the entire native IBABP-L exon 1-3 polynucleotide, or the full-length protein-coding sequence of a native IBABP-L mRNA or cDNA, wherein the isolated polynucleotide hybridizes selectively to the native IBABP-L polynucleotide.

According to another embodiment of the invention, isolated polynucleotides are provided that (a) encode a polypeptide of at least 11 amino acids, wherein the polypeptide comprises at least 4 contiguous amino acids of a native IBABP-L N-terminal polypeptide, and, (b) when introduced into a mammal, elicits an antibody that binds selectively to a native IBABP-L polypeptide. In one such embodiment, the polypeptide comprises at least 5, 6, 7, 8, 9, or 10 contiguous amino acids of the IBABP-L N-terminal polypeptide.

According to another embodiment of the invention, any of the above-mentioned isolated polynucleotides encodes a polypeptide that binds bile acid.

Also provided are cells, vectors (including expression vectors), probes and primers that comprise any of the above-mentioned polynucleotides, as well as cells comprising such vectors.

According to another embodiment of the invention, kits are provided that comprise (a) a first primer comprising at least 15 contiguous nucleotides of a native IBABP-L exon 1-3 polynucleotide, wherein the first primer hybridizes selectively to a native IBABP-L polynucleotide; (b) a second primer comprising at least 15 contiguous nucleotides from the native IBABP-L polynucleotide; and (c) suitable packaging enclosing the first primer and the second primer, wherein an amplification reaction performed using the first primer, the second primer, and a sample comprising an IBABP-L mRNA produces an amplification product that indicates the presence of the IBABP-L mRNA in the sample. According to one embodiment of such kits, the second primer hybridizes selectively to the IBABP-L exon 1-3 polynucleotide.

Such kits also optionally comprise a third primer comprising at least 15 contiguous nucleotides from a native IBABP polynucleotide; an amplification reaction performed using the first, second and third primers and the sample produces a first amplification product that indicates the presence of IBABP-L mRNA in the sample and a second amplification product that indicates the presence of IBABP mRNA in the sample. The third primer in such kits optionally comprises at least 15 contiguous nucleotides from a native IBABP exon 4a polynucleotide.

Such kits also optionally comprise a fourth primer. According to one embodiment, the third primer comprises at least 15 contiguous nucleotides from a native IBABP polynucleotide, and the fourth primer comprises at least 15 contiguous nucleotides from the native IBABP polynucleotide. A polymerase chain reaction performed using the first, second, third and fourth primer and the sample produces a first amplification product that indicates the presence of the IBABP-L mRNA in the sample and a second amplification product that indicates the presence of the IBABP mRNA in the sample. Optionally, the third primer or the fourth primer comprises at least 15 contiguous nucleotides from a native IBABP exon 4a polynucleotide.

According to another embodiment of the invention, isolated polypeptides are provided that comprise a sequence (optionally having a length of 15, 20, 30, or 40 or more amino acid residues) that has at least 90%, 95%, 99%, or 100% amino acid sequence identity to a native IBABP N-terminal polypeptide, wherein introduction of the isolated polypeptide into a mammal elicits production of an antibody that selectively binds to IBABP-L.

According to another embodiment of the invention, isolated polypeptides are provided that comprise a sequence of at least 11, 12, 13, 15, 20, 30 contiguous amino acids from an IBABP-L N-terminal polypeptide, or the IBABP-L N-terminal polypeptide, or the native IBABP-L polypeptide, wherein introduction of the isolated polypeptide into a mammal elicits production of an antibody that selectively binds to IBABP-L. According to one such embodiment of the invention, the isolated polypeptide binds bile acid.

According to another embodiment of the invention, isolated polypeptides at least 11 amino acid residues in length are provided that comprise at least 4, 5, 6, 7, 8, 9, 10, 12, or 15 contiguous amino acids of a native IBABP-L N-terminal polypeptide, wherein introduction of the isolated polypeptide into a mammal elicits production of an antibody that binds selectively to the native IBABP-L polypeptide.

According to another embodiment of the invention, pharmaceutical compositions are provided that comprise an amount of an IBABP-L polypeptide that is effective to treat or prevent colorectal cancer and a pharmaceutically acceptable carrier.

According to another embodiment of the invention, methods are provided for making a medicament for treating a patient with colorectal cancer or at risk for developing colorectal cancer, such methods comprising formulating the medicament with a pharmaceutically effective amount of an IBABP-L polypeptide.

According to another embodiment of the invention, methods are provided for treating or preventing colorectal cancer comprising administering to a patient in need thereof a composition comprising an effective amount of an IBABP-L polypeptide.

According to another embodiment of the invention, polyclonal, monoclonal, chimeric, humanized, single-chain, and fragment antibodies are provided that bind selectively to a native IBABP-L polypeptide.

According to another embodiment of the invention, methods are provided for making an antibody that binds selectively to a native IBABP-L polypeptide comprising introducing into a mammal (a) an expression vector comprising any of the above-mentioned isolated polynucleotides or (b) any of the above-mentioned isolated polypeptides, thereby eliciting production of an the antibody.

Also provided by the present invention are various methods for identifying the presence of, or measuring, an IBABP-L polypeptide or polynucleotide in a sample; for determining the ratio of IBABP-L polypeptide to IBABP polypeptide; and for determining the ratio of IBABP-L polynucleotide (e.g., mRNA) to IBABP polynucleotide in a sample. Such methods are useful for a variety of purposes, including, but not limited to: detecting the presence of a colorectal cancer in an individual; assessing the progress of a course of treatment for a patient suffering from colorectal cancer; identifying an individual who is at increased risk to develop colorectal cancer; identifying an individual who is likely to respond to a particular therapy for colorectal cancer; etc. In methods in which is made a measurement of IBABP-L polynucleotide or polypeptide in a sample, or the IBABP-L/IBABP polynucleotide or polypeptide ratio in a sample, the measurement can be compared to a reference, e.g., a similar measurement from a control sample from the individual, a measurement from the individual taken at one or more different timepoints (e.g., a baseline measurement before commencing therapy or a measurement at one or more timepoints during and/or after a course of therapy); a value derived from measurements taken from a population of individuals who are healthy, suffer from various stages of colorectal cancer, are at enhanced risk of developing colorectal cancer, etc.; and other such reference values.

Therefore, according to another embodiment of the invention, methods are provided for detecting the presence of an IBABP-L polypeptide in a sample comprising the IBABP-L polypeptide, such methods comprising contacting the sample with an antibody according to the present invention that binds selectively to the IBABP-L polypeptide, and detecting binding of the antibody to the IBABP-L polypeptide. Examples of assays that embody such methods include but are not limited to ELISA and bio-barcode assays. According to one such embodiment, the IBABP-L polypeptide in the sample is measured (i.e., performed quantitatively), e.g., by measuring binding of the antibody to the polypeptide in the sample.

According to another embodiment of the invention, methods are provided for determining a ratio of IBABP-L polypeptide to IBABP polypeptide in a sample from the individual that comprises IBABP-L polypeptide and IBABP polypeptide. One such embodiment comprises: (a) contacting the sample with a first antibody that binds selectively to the IBABP-L polypeptide, and measuring binding of the first antibody to the IBABP-L polypeptide in the sample; (b) contacting the sample with a second antibody that binds selectively to IBABP polypeptide and to IBABP-L polypeptide, and measuring binding of the second antibody to the IBABP polypeptide and the IBABP-L polypeptide in the sample; and (c) calculating the ratio of IBABP-L polypeptide to IBABP polypeptide in the sample. Steps (a) and (b) are optionally performed in a single reaction. Examples of such methods are ELISA or bio-barcode assays.

According to another embodiment of the invention, methods are provided for detecting the presence of an IBABP-L polynucleotide (e.g., mRNA) in a sample comprising the IBABP-L polynucleotide, such methods comprising contacting the sample with a probe or primer comprising a polynucleotide sequence that binds selectively to the IBABP-L polynucleotide and detecting binding of the probe or primer to the IBABP-L polynucleotide. In one such embodiment, the sample is contacted with a first primer that comprises the polynucleotide sequence that hybridizes selectively to the IBABP-L polynucleotide and a second primer comprising a polynucleotide sequence that hybridizes to the IBABP-L polynucleotide, an amplification reaction (such as a PCR reaction, e.g., a quantitative PCR or RT-PCR reaction) is performed, and an amplification product that indicates the presence of the IBABP-L polynucleotide in the sample is detected. As another embodiment, such methods comprise performing a bio-barcode assay. According to one such embodiment, the IBABP-L polynucleotide in the sample is measured (i.e., performed quantitatively), e.g., by measuring binding of the probe or primer to the polypeptide in the sample.

According to another embodiment of the invention, methods are provided for determining a ratio of IBABP-L mRNA to IBABP polynucleotide (e.g., mRNA) in a sample that comprises IBABP-L polynucleotide and IBABP polynucleotide. One such embodiment comprises (a) contacting the sample with a first probe that hybridizes selectively to a IBABP-L polynucleotide; (b) measuring hybridization of the first probe to the IBABP-L polynucleotide in the sample, (c) contacting the sample with a second probe that hybridizes selectively to IBABP polynucleotide and IBABP-L polynucleotide; (d) measuring hybridization of the second probe to the IBABP and IBABP-L polynucleotide in the sample; and (e) calculating the ratio of IBABP-L polynucleotide to IBABP polynucleotide in the sample. Another such embodiment comprises (1) contacting the sample with at least one primer that hybridizes selectively to IBABP-L polynucleotide and performing a first amplification reaction (e.g., PCR, including without limitation RT-PCR) to produce a first amplification product that indicates the presence of the IBABP-L polynucleotide in the sample; (b) contacting the sample with at least one primer that hybridizes selectively to IBABP and IBABP-L polynucleotide and performing a second amplification reaction to produce a second amplification product that indicates the presence of IBABP and IBABP-L polynucleotide in the sample; (c) measuring the first amplification product and the second amplification product; (d) calculating the ratio of IBABP-L polynucleotide to IBABP polynucleotide in the sample. In such methods the steps of contacting and of performing amplification reactions are optionally performed in a single reaction. Another such embodiment employs a bio-barcode assay.

According to another embodiment of the invention, methods are provided for detecting a colorectal cancer in an individual, or identifying an individual who is at increased risk to develop colorectal cancer, or identifying an individual who is likely to respond to a particular therapy for colorectal cancer. Such methods comprise measuring IBABP-L polypeptide in a sample from the individual that comprises the IBABP-L polypeptide. One such embodiment comprises measuring a ratio of IBABP-L polypeptide to IBABP polypeptide in a sample from the individual that comprises the IBABP-L polypeptide and the IBABP polypeptide. Another such embodiment comprises measuring IBABP-L mRNA in a sample from the individual that comprises the IBABP-L mRNA. Another such embodiment comprises measuring a ratio of IBABP-L mRNA to IBABP mRNA in a sample from the individual that comprises the IBABP-L mRNA and the IBABP mRNA.

According to another embodiment of the invention, methods are provided for assessing the progress of a course of treatment for a patient suffering from colorectal cancer. Such methods comprise measuring IBABP-L polypeptide, IBABP-L mRNA, the ratio of IBABP-L polypeptide to IBABP polypeptide, or the ratio of IBABP-L mRNA to IBABP mRNA in samples taken from the patient at different timepoints during the course of treatment and comparing the measurements from the samples from the various timepoints.

In any of the foregoing methods, the samples employed include cells, tissues (e.g., a gastrointestinal tissue sample), fecal (stool) samples, a body fluid (e.g., blood) or any other suitable sample. As mentioned above, any measurements taken of IBABP-L polypeptide or polynucleotide or IBABP-L/IBABP polypeptide or polynucleotide ratios in any of the foregoing methods optionally may be compared to a suitable reference. Any of the foregoing methods optionally may be automated.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE FIGURES

FIG. 1 shows the structure of IBABP-L (fabp6) with exons (E1-E7) and proposed promoters (P1 and P2) labeled (not drawn to scale). P1 drives the expression of IBABP-L, a new variant identified herein (Example 1), which contains seven exons, the first three of which are unique to IBABP-L. P2 promotes the transcription of IBABP, the known form of IBABP, which shares exon 4b to exon 7 with IBABP-L.

FIG. 2 shows the open reading frame of the IBABP gene (SEQ ID NO: 1) (i.e., genomic sequence), which encodes both IBABP-L and IBABP. The open reading frame of IBABP (the 14 kDa form) is underlined, with the additional open reading frame sequence for IBABP-L highlighted in grey. Thus, the open reading frame for IBABP-L contains much of the ORF for IBABP, but also an additional 627 nucleotides on the 5' end of the gene. The poly(A) signal is bold and underlined.

FIG. 3 shows DNA sequences from the IBABP gene that are unique to IBABP-L (SEQ ID NO: 2) (highlighted in gray in FIG. 2).

FIG. 4 shows an alignment of cDNA sequences for IBABP-L and IBABP. The cDNA sequence for IBABP-L (top line) (SEQ ID NO: 3) is shown with the ATG start site noted in bold. The cDNA sequence for IBABP (bottom line) (SEQ ID NO: 4) are highlighted in gray. Exons 1, 2 and 3 are unique to IBABP-L (note dashes showing a lack of any homologous exon for IBABP). Exon 4a (underlined) is present only in the cDNA for IBABP. Exons 4b-7 are shared by the cDNAs for both IBABP-L and IBABP.

FIG. 5 shows the cDNA sequence encoding IBABP-L (SEQ ID NO: 5).

FIG. 6 shows the nucleotide sequence encoding the N-terminal 49 amino acid sequence from the IBABP-L cDNA (SEQ ID NO: 6).

FIG. 7 shows an alignment of polypeptide sequences for IBABP-L (top line) (SEQ ID NO: 7) and IBABP (bottom line, highlighted in gray) (SEQ ID NO: 8). IBABP-L polypeptide contains a 49 amino acid sequence at its N-terminus that is absent from the IBABP polypeptide.

DETAILED DESCRIPTION OF THE INVENTION

Figures 8, 9:
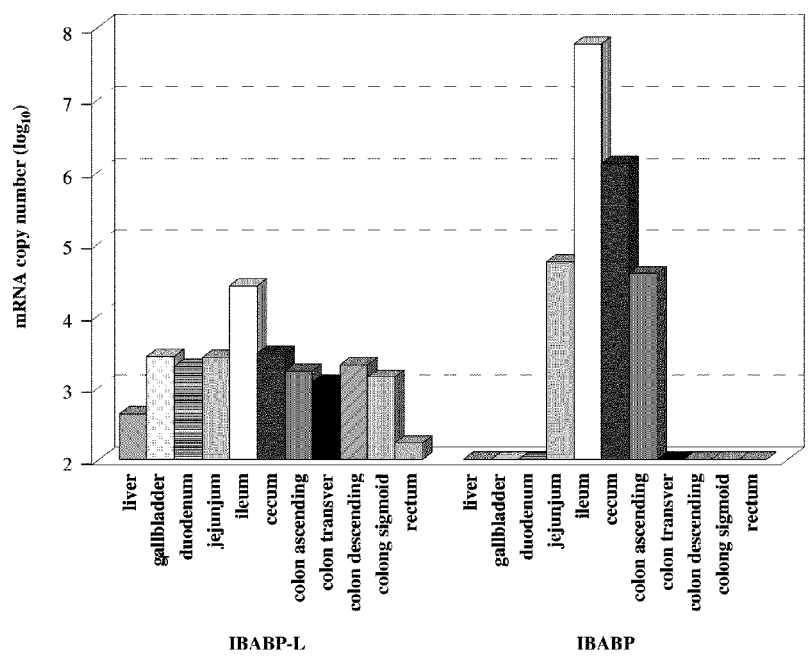
FIG. 8 shows the predicted polypeptide sequence of IBABP-L (SEQ ID NO: 9). The 49 amino acid N-terminal sequence of IBABP-L that is not found in the IBABP polypeptide is highlighted in gray.
FIG. 9 shows expression of IBABP and IBABP-L in the gastrointestinal tract. RNA extracted from human liver, gallbladder, and sections of the gastrointestinal tract (duodenum through rectum) was used as a template in quantitative RT-PCR aimed at quantifying IBABP and IBABP-L. The expression of each variant was normalized using housekeeping gene ARPP0.

We have identified a new variant of IBABP and designated it as IBABP-L. The transcript for IBABP-L arises from an alternative start site and includes three exons that are absent in IBABP. IBABP-L also shares part of a fourth exon with IBABP. The protein encoded by IBABP-L contains a unique 49 amino acid-long N-terminal sequence that is not shared by the IBABP polypeptide.

The IBABP-L transcript is expressed at similar levels throughout the normal human intestine. This is in contrast to the transcript encoding IBABP, which is expressed at levels several orders of magnitude higher in the section of the intestine extending from the jejunum to the ascending colon. In these regions of the intestine, the expression of IBABP-L is at least an order of magnitude lower than IBABP. The two transcripts also differ in their response to bile acids. While bile acids stimulate the expression of IBABP as part of the FXR transcription pathway (Grober et al., J. Biol. Chem. 274:29749-29754, 1999), they are without effect on the expression of IBABP-L.

We compared the expression of IBABP and IBABP-L in colorectal carcinoma samples from 68 patients. IBABP remains essentially unchanged in colorectal cancer, but IBABP-L is up-regulated. In most cases the up-regulation is substantial, with the mean increase in relative mRNA copy number being greater than 30-fold. IBABP-L is up-regulated in early malignant polyps and its high expression is evident in all subsequent clinical classifications of tumor differentiation. Although a trend toward up-regulation in colorectal cancer is evident with PCR primers that fail to distinguish between the two transcripts, a specific measure of IBABP-L is far more sensitive.

Three other factors are important to consider in the use of IBABP-L as a potential biomarker. First, the increase in IBABP-L expression in colorectal cancer is independent of the patients' age or gender. Second, based on studies in colon cancer cells lines, the expression of IBABP-L appears to be independent of common oncogenic mutations to proteins like p53, APC, or K-ras. Nevertheless, in conjunction with the fact that IBABP-L is up-regulated in most tumors, the studies from cell lines show that it is highly unlikely that the expression of IBABP-L is dependent on a lesion in a single oncogene. Third, unlike IBABP, the expression of IBABP-L is not influenced by bile acids. Therefore, one would not expect the levels of IBABP-L to be tied to changes in bile acids resulting from dietary changes or overall health status. Collectively, the expression of IBABP-L has many properties that make it well suited for use as a broadly applicable test for colorectal cancer.

We found that the ratio of expression between IBABP-L and IBABP ($R_C/R_N$) in samples is a slightly better predictor of colorectal cancer than the relative levels of IBABP-L alone.

IBABP and Cholesterol Metabolism

Cholesterol is a multifunctional molecule that is essential for a broad array of physiologic processes including membrane biogenesis, caveolae formation, and the distribution of embryonic signaling molecules. It is also as an essential precursor in the synthesis of transcriptionally active lipids including the steroid hormones and oxysterols (Brown and Goldstein, Cell 89:331-340, 1997). Although essential, cholesterol is highly insoluble and can form deposits that contribute to a variety of diseases including gallstones and heart disease (Dowling, Aliment Pharmacol. Ther. 14 Suppl. 2:39-47, 2000; Jones, Am. J. Manag. Care. 7:S289-S298, 2001).

Cholesterol levels are controlled at a variety of levels including intestinal uptake, endogenous biosynthesis, transport, and elimination. The major pathway for cholesterol elimination is via hepatic conversion of cholesterol into water-soluble bile acids (Chiang, Front. Biosci. 3:D176-D193, 1998) and their subsequent secretion into the gastrointestinal tract. Approximately 95% of the secreted bile acids are recycled via intestinal uptake and are returned to the liver through the portal blood. The remaining 5% of bile acids are eliminated from the gut thereby forcing the liver to replenish these losses by converting as much as 0.5 g of cholesterol to bile acids each day (Russell, Cell 97:539-542, 1999). The liver therefore has an enormous capacity to metabolize cholesterol and therapies that target this process have the potential to eliminate cholesterol derived from a variety of sources including diet, synthesis, and atherosclerotic lesions (via the reverse cholesterol transport pathway).

Two metabolic pathways have been identified that convert cholesterol to bile acids (Chiang, Front. Biosci. 3:D176-D193, 1998). In humans, the classic pathway is responsible for at least 90% of all bile acid synthesis. The first and rate-limiting step in this pathway is catalyzed by CYP7A1,[1] a liver-specific cholesterol 7α-hydroxylase. CYP7A1 transcription is strongly repressed by its bile acid end products (Myant et al., J. Lipid Res. 18:135-153, 1977). A member of the nuclear receptor superfamily (FXR, NR1H4, hereafter referred to as BAR) suppresses CYP7A1 transcription in response to endogenous bile acids (Wang et al., Mol. Cell 3:543-553, 1999; Makishima et al., Science 284:1362-1365, 1999; Parks et al., Science 284:1365-1368, 1999; Sinal et al., Cell 102:731-744, 2000). Two bile acid response elements (BAREs) have been identified in the CYP7A1 promoter. However, BAR is unable to bind directly to either element, suggesting an indirect role for BAR in the regulation of CYP7A1 (Chiang et al., J. Biol. Chem. 275:10918-10924, 2000). A mechanism has been proposed whereby BAR induces the negative transcriptional regulator SHP (small heterodimer partner), which in turn represses transcription factors that bind to the CYP7A1 BAREs (Lu et al., Mol. Cell 6:507-515, 2000; Goodwin et al., Mol. Cell 6:517-526, 2000). This mechanism for CYP7A1 repression was suggested based on experiments using transiently overexpressed SHP. Because SHP can repress (Lee et al., Mol. Cell. Biol. 20:187-195, 2000; Seol et al., Mol. Endocrinol. 12:1551-1557, 1998) and/or activate (Nishizawa et al., J. Biol. Chem. 277:1586-1592, 2002) numerous nuclear receptors under these conditions, the SHP-induction model does not account for the specificity by which bile acids regulate gene transcription.

Although the mechanisms underlying transrepression by BAR is unclear, it is well known that BAR activates transcription by binding to specific response elements (Forman et al., Cell 81, 687-693, 1995; Laffitte et al., J. Biol. Chem. 275: 10638-10647, 2000) as a heterodimer with the nuclear receptor RXR. Several genes have been identified whose transcription is activated by BAR including SHP, the ileal bile acid-binding protein (IBABP), and the hepatic bile salt export pump (BSEP, ABCB11) (Edwards et al., J. Lipid Res. 43:2-12, 2002). These genes are critical for bile acid homeostasis. IBABP is an intracellular protein expressed in the distal ileum where the majority of bile acids are reabsorbed. It has been proposed that IBABP plays a role in transcellular shuttling and/or buffering the high and otherwise toxic levels of bile acids that pass through this tissue. BSEP is a canalicular ATP binding cassette transporter that is responsible for biliary secretion of bile acids. Indeed, inactivating mutations of this gene result in progressive familial intrahepatic cholestasis (type 2) and hepatic cirrhosis (Strautnieks et al., Nat. Genet. 20:233-238, 1998). Thus, in addition to regulating cholesterol degradation, BAR plays a more general role in coordinately regulating bile acid physiology.

BAR also controls other aspects of lipid homeostasis. For example, BAR agonists reduce triglyceride levels (Iser and SalI, Drugs 21:90-119, 1981; Maloney et al., J. Med. Chem. 43, 2971-2974, 2000) and BAR-null mice have elevated triglycerides (Sinal et al., Cell 102:731-744, 2000). This is potentially related to BAR-mediated regulation of apolipoprotein CII and/or phospholipid transfer protein (reviewed in Edwards et al., J. Lipid Res. 43:2-12, 2002). Regardless of the mechanism, it appears that BAR activation promotes reciprocal effects on cholesterol and triglyceride levels. Two classes of BAR modulators have been identified (Dussault et al., J. Biol. Chem. 278:7027-7033, 2003). The first class include agonists that are ~25-fold more potent than naturally occurring bile acids. These compounds activate BAR and produce the expected regulation pattern on endogenous target genes. AGN34 has been identified as a gene-selective BAR modulator (BARM): it acts as an agonist on CYP7A1, an antagonist on IBABP, and is neutral on SHP (Dussault et al., J. Biol. Chem. 278:7027-7033, 2003).

DEFINITIONS AND METHODS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 CFR 1.822 is used. The standard one- and three-letter nomenclature for amino acid residues is used.

Polynucleotides

The transcript (mRNA) for IBABP-L arises from an alternative start site from the start site for the transcript for IBABP. The IBABP-L transcript includes sequences corresponding to three exons (exons 1-3 of the IBABP gene) that are absent from the IBABP transcript and that encode the 49 amino acid sequence at the amino (N) terminus of the IBABP-L polypeptide. Thus, sequences from exons 1-3 are unique to IBABP-L and are useful for producing probes and primers for identifying and quantifying IBABP-L polynucleotides and for other purposes.

As used herein, the term "IBABP-L exon 1-3 polynucleotide (or probe or primer)" refers to a polynucleotide (or probe or primer) that consists of sequences corresponding to exons 1, 2 and 3 from the IBABP gene and that are absent from the IBABP transcript, i.e., the coding region for the 49 amino acid IBABP-L N-terminal polypeptide (as defined below).

As used herein, the term "IBABP-L polynucleotide" refers to this IBABP-L mRNA and the corresponding cDNA, including but not limited to the protein-coding region thereof. Also encompassed by the term "IBABP-L polynucleotides" are, for example: fragments or portions of the IBABP-L mRNA or cDNA, including but not limited to, an IBABP-L exon 1-3 polynucleotide; fragments that encode antigenic determinants of IBABP-L (e.g., those that elicit antibodies that bind selectively to IBABP-L polypeptide); probes and primers that hybridize selectively to IBABP-L polynucleotides; etc. Also included are mutated or variant polynucleotides that include one or more nucleotide insertions, deletions, or substitutions from the wild-type IBABP-L sequence, but that, for example: retain the ability to bind selectively to IBABP-L; encode a polypeptide that includes an IBABP-L antigenic determinant; encode a polypeptide having IBABP-L activity; etc.

As used herein, the term "hybridizes selectively" refers to binding of a probe, primer or other polynucleotide, under stringent hybridization conditions, to a target polynucleotide, such as a native, or wild-type, IBABP-L mRNA or cDNA, to a substantially higher degree than to other polynucleotides. Probes and primers that hybridize selectively to IBABP-L include sequences that are unique to IBABP-L, i.e., exons 1-3. In particular, a probe that "hybridizes selectively" to IBABP-L does not hybridize substantially to IBABP under stringent hybridization conditions and therefore can be used to distinguish an IBABP-L polynucleotide (e.g., an IBABP mRNA) from an IBABP polynucleotide. Similarly, a primer that "hybridizes selectively" to IBABP-L, when used in an amplification reaction such as PCR, results in amplification of IBABP-L without resulting in substantial amplification of IBABP under suitable amplification conditions. Thus, all or substantially all of an IBABP-L-selective probe or primer hybridizes to the target IBABP-L polynucleotide under suitable conditions, as can be determined given the sensitivity of a particular procedure. Similarly, as used herein, the term "selective for" in reference to a polynucleotide, indicates that the polynucleotide hybridizes selectively to a target polynucleotide.

Similarly, a probe or primer that includes a sequence that is unique to IBABP, such as a sequence from exon 4a (see FIG. 4), hybridizes selectively to IBABP. In particular, a probe that hybridizes selectively to IBABP does not hybridize substantially to IBABP under stringent hybridization conditions and therefore can be used to distinguish an IBABP polynucleotide (e.g., an IBABP mRNA) from an IBABP-L polynucleotide. Similarly, a primer that hybridizes selectively to an IBABP polynucleotide, when used in an amplification reaction such as PCR, results in amplification of the IBABP polynucleotide without resulting in substantial amplification of IBABP-L polynucleotide. Thus, all or substantially all of an IBABP-selective probe or primer hybridizes to the target IBABP polynucleotide, as can be determined given the sensitivity of a particular procedure.

As used herein, the term "native IBABP exon 4a polynucleotide (or probe or primer)" refers to a polynucleotide (or probe or primer) that consists of sequences corresponding to exon 4a from the IBABP gene and that are absent from the IBABP-L transcript.

Because sequences from IBABP mRNA are also present in IBABP-L mRNA, a polynucleotide sequence that hybridizes selectively to such shared sequences may also hybridize selectively to a sequence from an IBABP-L polynucleotide. Therefore, a probe or primer that includes sequences of sufficient length that are shared by IBABP and IBABP-L polynucleotides will hybridize under stringent hybridization conditions to both IBABP and IBABP-L, although such sequences do not hybridize to other polynucleotide sequences in a sample under stringent hybridization conditions and thus can be considered to bind "selectively" to IBABP and IBABP-L polynucleotides.

As used herein, the terms "wild-type" or "native" in reference to a polynucleotide are used interchangeably to refer to a polynucleotide that has 100% sequence identity with a reference polynucleotide that can be found in a cell or organism, or a fragment thereof.

Polynucleotide (e.g., DNA or RNA) sequences may be determined by sequencing a polynucleotide molecule using an automated DNA sequencer. A polynucleotide sequence determined by this automated approach can contain some errors. The actual sequence can be confirmed by resequencing the polynucleotide by automated means or by manual sequencing methods well known in the art.

Unless otherwise indicated, each "nucleotide sequence" set forth herein is presented as a sequence of deoxyribonucleotides (abbreviated A, G, C and T). However, the term "nucleotide sequence" of a DNA molecule as used herein refers to a sequence of deoxyribonucleotides, and for an RNA molecule, the corresponding sequence of ribonucleotides (A, G, C and U) where each thymidine deoxynucleotide (T) in the specified deoxynucleotide sequence in is replaced by the ribonucleotide uridine (U).

By "isolated" polynucleotide is intended a polynucleotide that has been removed from its native environment For example, recombinant polynucleotides contained in a vector are considered isolated for the purposes of the present invention. Further examples of isolated polynucleotides include recombinant polynucleotides maintained in heterologous host cells or purified (partially or substantially) polynucleotides in solution. Isolated RNA molecules include in vivo or in vitro RNA transcripts of the DNA molecules of the present invention. Isolated polynucleotides according to the present invention further include such molecules produced synthetically.

Polynucleotides can be in the form of RNA, such as mRNA, or in the form of DNA, including, for instance, cDNA and genomic DNA. The DNA can be double-stranded or single-stranded. A single-stranded DNA or RNA can be a coding strand, also known as the sense strand, or it can be a non-coding strand, also referred to as the anti-sense strand. Polynucleotides can include non-naturally occurring nucleotide or ribonucleotide analogs.

The term "fragment" (of a polynucleotide) as used herein refers to polynucleotides that are part of a longer polynucleotide having a length of at least about 15, 20, 25, 30, 35, or 40 nucleotides (nt) in length, which are useful, for example, as probes and primers. A polynucleotide consisting of a sequence that includes all or part of exons 1-3 of the IBABP-L cDNA (i.e., the sequences that encode the 49 amino acid N-terminal polypeptide of IBABP-L), or a portion thereof, would be considered a fragment of the full-length IBABP-L cDNA, for example. Thus, for example, a fragment of IBABP-L at least 20 nucleotides in length includes 20 or more contiguous bases from the nucleotide sequence of the IBABP-L full-length cDNA. Such DNA fragments may be generated by the use of automated DNA synthesizers or by restriction endonuclease cleavage or shearing (e.g., by sonication) a full-length IBABP-L cDNA, for example.

Also encompassed by the present invention are isolated polynucleotides that hybridize under stringent hybridization conditions to an IBABP-L polynucleotide such as, for example, an IBABP-L transcript (i.e., mRNA). By "stringent hybridization conditions" is intended overnight incubation at 42° C. in a solution comprising: 50% formamide, 5×SSC (750 mM NaCl, 75 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. Alternatively, stringent hybridizations are conditions used for performance of a polymerase chain reaction (PCR). Such hybridizing polynucleotides are useful diagnostically as a probe according to conventional DNA hybridization techniques or as primers for amplification of a target sequence by the polymerase chain reaction (PCR).

As used herein, the term "hybridizes (or binds) specifically" is used interchangeably with the term "hybridizes (or binds) selectively" means that most or substantially all hybridization of a probe or primer is to a particular polynucleotide in a sample under stringent hybridization conditions.

The present invention also provides polynucleotides that encode all or a portion of a polypeptide, e.g., a full-length IBABP-L polypeptide or a portion thereof. Such protein-coding polynucleotides may include, but are not limited to, those sequences that encode the amino acid sequence of the particular polypeptide or fragment thereof and may also include together with additional, non-coding sequences, including for example, but not limited to introns and non-coding 5' and 3' sequences, such as the transcribed, non-translated sequences that play a role in transcription, mRNA processing—including splicing and polyadenylation signals, e.g., ribosome binding and stability of mRNA; an additional coding sequence which codes for additional amino acids, such as those which provide additional functionalities. In addition, the sequence encoding the polypeptide can be fused to a heterogeneous polypeptide or peptide sequence, such as, for example a marker sequence that facilitates purification of the fused polypeptide. One example of such a marker sequence is a hexa-histidine peptide, such as the tag provided in a pQE vector (Qiagen, Inc.). As described in Gentz et al., Proc. Natl. Acad. Sci. USA 86:821-824 (1989), for instance, hexa-histidine provides for convenient purification of the fusion protein. The "HA" tag is another peptide useful for purification which corresponds to an epitope derived from the influenza hemagglutinin (HA) protein, which has been described by Wilson et al., Cell 37:767 (1984).

The present invention further relates to variants of the native, or wild-type, polynucleotides of the present invention, which encode portions, analogs or derivatives of an IBABP-L polypeptide. Variants can occur naturally, such as a natural allelic variant, i.e., one of several alternate forms of a gene occupying a given locus on a chromosome of an organism. Non-naturally occurring variants can be produced, e.g., using known mutagenesis techniques or by DNA synthesis. Such variants include those produced by nucleotide substitutions, deletions or additions. The substitutions, deletions or additions can involve one or more nucleotides. The variants can be altered in coding or non-coding regions or both. Alterations in the coding regions can produce conservative or non-conservative amino acid substitutions, deletions or additions. Also included are silent substitutions, additions and deletions, which do not alter the properties and activities of the IBABP-L polypeptide or portions thereof.

Further embodiments of the invention include isolated polynucleotide molecules have, or comprise a sequence having, a high degree of sequence identity with a native, or wild type, IBABP-L polynucleotide, for example, at least 90%, 95%, 96%, 97%, 98% or 99% identical thereto.

A polynucleotide is considered to have a nucleotide sequence at least, for example, 95% "identical" to a reference nucleotide sequence if it is identical to the reference sequence except that it includes up to five mutations (additions, deletions, or substitutions) per each 100 nucleotides of the reference nucleotide sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence. Nucleotide sequence identity may be determined conventionally using known computer programs such as the BESTFIT program (Wisconsin Sequence Analysis Package, Version 8 for Unix, Genetics Computer Group, University Research Park, 575 Science Drive, Madison, Wis. 53711. BESTFIT uses the local homology algorithm of Smith and Waterman, Adv. Appl. Math. 2:482-489 (1981), to find the best segment of homology between two sequences. When using BESTFIT or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Recombinant Constructs; Vectors and Host Cells

The present invention also provides recombinant polynucleotide constructs that comprise an IBABP-L polynucleotide, including but not limited to vectors. The present invention also provides host cells comprising such vectors and the production of IBABP-L polypeptides or fragments thereof by recombinant or synthetic techniques.

"Operably Linked". A first nucleic-acid sequence is "operably linked" with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" polynucleotide is made by an artificial combination of two otherwise separated segments of sequence, e.g., by chemical synthesis or by the manipulation of isolated segments of polynucleotides by genetic engineering techniques. Techniques for nucleic-acid manipulation are well-known (see, e.g., Sambrook et al., 1989, and Ausubel et al., 1992). Methods for chemical synthesis of polynucleotides are discussed, for example, in Beaucage and Carruthers, Tetra. Letts. 22:1859-1862, 1981, and Matteucci et al., J. Am. Chem. Soc. 103:3185, 1981. Chemical synthesis of polynucleotides can be performed, for example, on commercial automated oligonucleotide synthesizers.

Recombinant vectors are produced by standard recombinant techniques and may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

Expression vectors include sequences that permit expression of a polypeptide encoded by a polynucleotide of interest in a suitable host cell. Such expression may be constitutive or non-constitutive, e.g., inducible by an environmental factor or a chemical inducer that is specific to a particular cell or tissue type, for example. Expression vectors include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

In expression vectors, a polynucleotide insert is operably linked to an appropriate promoter. The promoter may be a homologous promoter, i.e., a promoter or functional portion thereof, that is associated with the polynucleotide insert in nature, for example, an IBABP promoter with an IBABP or IBABP-L protein coding region. Alternatively, the promoter may be a heterologous promoter, i.e., a promoter or functional portion thereof, that is not associated with the polynucleotide insert in nature, for example, a bacterial promoter used for high-level protein expression in bacterial cells (or, for that matter, any promoter other than an IBABP promoter) operably linked to an IBABP-L protein coding region. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vectors may include one or more selectable marker suitable for selection of a host cell into which such a vector has been introduced. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture media and conditions for the above-described host cells are known in the art.

Bacterial promoters suitable include the *E. coli* lad and lacZ promoters, the T3 and T7 promoters, the gpt promoter, the lambda PR and PL promoters and the trp promoter. Eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

A polypeptide of interest may be expressed in a modified form, such as a fusion protein, and may include not only secretion signals but also additional heterologous functional regions. For instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

An expressed polypeptide of interest can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polypeptides

As used herein, the phrase "an IBABP-L polypeptide" refers to a polypeptide at least 10, 11, 12, 12, 14, 15, 20, 30, 40, 49, 50, 100 or more amino acid residues in length and have a high degree of sequence identity with the full-length native, or wild-type, IBABP-L polypeptide or a fragment thereof.

Included are variant forms of IBABP-L polypeptides that include deletions, insertions or substitutions of one or more amino acid residues in a native IBABP polypeptide sequence, including without limitation polypeptides that exhibit activity similar, but not necessarily identical, to an activity of the full-length native, or wild-type, IBABP-L polypeptide or fragment thereof as measured in a relevant biological assay.

As used herein, the terms "wild-type" or "native" in reference to a peptide or polypeptide are used interchangeably to refer to a polypeptide that has 100% sequence identity with a reference polypeptide that can be found in a cell or organism, or a fragment thereof.

As used herein, the term "N-terminal polypeptide of IBABP-L," or "IBABP-L N-terminal polypeptide," or simply "N-terminal polypeptide" refers to a unique 49-amino acid sequence at the N-terminus of the IBABP-L polypeptide, which is not part of the IBABP polypeptide.

As used herein, the terms "peptide" and "oligopeptide" are considered synonymous and, as used herein, each term refers to a chain of at least two amino acids coupled by peptidyl linkages. As used herein, the terms "polypeptide" and "protein" are considered synonymous and each term refers to a chain of more than about ten amino acid residues. All oligopeptide and polypeptide formulas or sequences herein are written from left to right and in the direction from amino terminus to carboxy terminus.

As used herein, the term "isolated" polypeptide or protein refers to a polypeptide or protein removed from its native environment. For example, recombinantly produced polypeptides and proteins expressed in host cells are considered isolated for purposes of the invention as are native or recombinant polypeptides and proteins which have been substantially purified by any suitable technique.

As used herein, the term "binds selectively" is interchangeable with the term "binds specifically, and, when used in reference to an IBABP polypeptide, refers to binding of an antibody, ligand, receptor, substrate, or other binding agent to the target IBABP polypeptide to a substantially higher degree than to other polypeptides, such as, for example, to IBABP. According to some embodiments, all or substantially all binding of an antibody or other binding agent is to the target IBABP-L polynucleotide, as can be determined given the sensitivity of a particular procedure. An antibody, ligand, receptor, substrate or other binding agent is said to be "selective for" or specific for" a polypeptide or other target molecule, such as IBABP-L, if it binds selectively to the target molecule.

The amino acid sequence of an IBABP-L polypeptide or peptide can be varied without significant effect on the structure or function of the protein. In general, it is possible to replace residues which contribute to the tertiary structure of the polypeptide or peptide, provided that residues performing a similar function are used. In other instances, the type of residue may be completely unimportant if the alteration occurs at a non-critical region of the protein.

Thus, the invention further includes variations of IBABP-L polypeptide or peptide that show substantial IBABP-L activity. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Guidance concerning which amino acid changes are likely to be phenotypically silent (i.e., are not likely to have a significant deleterious effect on a function) can be found, for example, in Bowie et al., Science 247:1306-1310, 1990.

Thus, a fragment, derivative or analog of a native, or wild-type IBABP-L polypeptide, may be (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence that is employed for purification of the mature polypeptide or a proprotein sequence.

Charged amino acids may be substituted with another charged amino acid. Charged amino acids may also be substituted with neutral or negatively charged amino acids, resulting in proteins with reduced positive charge. The prevention of aggregation is highly desirable to avoid a loss of activity and increased immunogenicity (Pinckard et al., Clin Exp. Immunol. 2:331-340, 1967; Robbins et al., Diabetes 36:838-845, 1987; Cleland et al., Crit. Rev. Therapeutic Drug Carrier Systems 10:307-377, 1993).

The replacement of amino acids can also change the selectivity of protein binding to cell surface receptors. Ostade et al., Nature 361:266-268 (1993) describes certain mutations resulting in selective binding of TNF-α to only one of the two known types of TNF receptors.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine. Conservative amino acid substitution within the native polypeptide sequence can be made by replacing one amino acid from within one of these groups with another amino acid from within the same group. In one aspect, biologically functional equivalents of the proteins or fragments thereof of the present invention can have ten or fewer, seven or fewer, five or fewer, four or fewer, three or fewer, two, or one conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, J. Mol. Biol. 157:105-132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, J. Mol. Biol. 157:105-132, 1982); these are: isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (4.5). In making such changes, the substitution of amino acids whose hydropathic indices may be within ±2, or ±1, or within ±0.5.

It is also understood in the art that the substitution of like amino acids can be made effectively on the basis of hydrophilicity. U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0.+−0.1), glutamate (+3.0.+−0.1), serine (+0.3), asparagine (+0.2), glutamine (+0.2), glycine (0), threonine (−0.4), proline (−0.5.+−0.1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4). In making changes to a native polypeptide or peptide sequence, the substitution of amino acids whose hydrophilicity values may be within ±2, or within ±1, or within ±0.5.

Of course, the number of amino acid substitutions a skilled artisan would make depends on many factors, including those described above. Generally speaking, the number of substitutions for any given IBABP-L polypeptide will not be more than 50, 40, 30, 20, 10, 5, 3, or 2.

Amino acids in the IBABP-L protein of the present invention that are essential for function can be identified by methods known in the art, such as site-directed mutagenesis or alanine-scanning mutagenesis (Cunningham and Wells, Science 244:1081-1085, 1989). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., J. Mol. Biol. 224:899-904, 1992; de Vos et al. Science 255:306-312, 1992).

The polypeptides and peptides of the present invention include native, or wild-type polypeptides and peptides, and polypeptides or peptide variants that are at least 75%, 80%, 85%, 90%, 95%, 96%, 97%, 98% or 99% identical to (or have such a degree of identity with) the native IBABP-L polypeptide and fragments thereof.

By a polypeptide having an amino acid sequence at least, for example, 95% "identical" to a reference amino acid sequence is intended that the amino acid sequence of the polypeptide is identical to the reference sequence except that the polypeptide sequence may include up to five amino acid alterations per each 100 amino acids of the reference amino acid sequence of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide has a particular degree of amino acid sequence identity when compared to a reference polypeptide can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another embodiment of the present invention, there are provided fragments of the polypeptides described herein. Such fragments include: a polypeptide comprising the 49-amino acid N-terminal sequence of IBABP-L; fragments that include one or more antigenic determinants of IBABP-L, for example, those that elicit antibodies that bind selectively to IBABP-L; and fragments of IBABP-L that bind bile acid. Also included are fragments that include both sequences that are unique to IBABP-L and that are shared by IBABP-L and IBABP. For example, one such fragment is a polypeptide that spans the junction between the 49-amino acid N-terminal sequence of IBABP-L and adjacent sequences in IBABP-L polypeptide (which are also present in IBABP) can be used to raise antibodies that bind specifically to the junction fragment, even if it includes as few as four to six amino acid residues from the N-terminal sequence of IBABP-L. Because such a junction fragment only exists and can be detected if sequences unique to IBABP-L are present, particularly sequences from the 49 amino acid N-terminal polypeptide, antibodies that are elicited by such junction fragments are considered to bind selectively to an IBABP-L polypeptide.

The polypeptide fragments of the present invention can be used for numerous purposes, for example, to elicit antibody production in a mammal, as molecular weight markers on SDS-PAGE gels or on molecular sieve gel filtration columns using methods well known to those of skill in the art, etc.

Polypeptides of the present invention can be used to raise polyclonal and monoclonal antibodies, which are useful in diagnostic assays for detecting IBABP-L expression or for other purposes. Further, such polypeptides can be used in the yeast two-hybrid system to "capture" binding proteins (Fields and Song, Nature 340:245-246, 1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998-4002, 1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., Science 219:660-666, 1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective (Sutcliffe et al., supra, at 661).

Antigenic epitope-bearing peptides and polypeptides of the invention are therefore useful to raise antibodies, including monoclonal antibodies, which bind selectively to a polypeptide of the invention. Thus, a high proportion of hybridomas obtained by fusion of spleen cells from donors immunized with an antigen epitope-bearing peptide generally secrete antibody reactive with the native protein (Sutcliffe et al., supra, at 663). The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for example, Wilson et al., Cell 37:767-778, 1984). The anti-peptide antibodies of the invention also are useful for protein purification, e.g., by adsorption chromatography using known methods.

Antigenic epitope-bearing peptides and polypeptides of the invention designed according to the above guidelines may contain a sequence of at least 7, 8, 9, 10, 11, 12, 13, 14, 15, 20 or 30 or more amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein.

According to one embodiment of the invention, peptides and polypeptides are provided that span the junction between the 49 amino acid N-terminal polypeptide and the remainder of the IBABP-L polypeptide, i.e., that include both unique sequences from IBABP-L (e.g., 4, 5, 6, 7, 8, 9, 10 or more contiguous amino acid residues from the 49 amino acid N-terminal polypeptide of IBABP-L) and sequences that are included in both the IBABP-L and IBABP polypeptides. Such junction-spanning peptides and polypeptides can be used to elicit the production of antibodies in a mammal (e.g., mouse, rat, rabbit, human, etc.) that bind selectively to IBABP-L polypeptide.

The amino acid sequence of the epitope-bearing peptide may be selected to provide substantial solubility in aqueous solvents (i.e., sequences including relatively hydrophilic residues and highly hydrophobic sequences may be avoided).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HAI polypeptide which were prepared and characterized (by binding studies employing an enzyme-linked immunosorbent assay [ELISA]) in less than four weeks (Houghten, Proc. Natl. Acad. Sci. USA 82:5131-5135, 1985; and U.S. Pat. No. 4,631,211). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously.

Epitope-bearing peptides and polypeptides of the invention are used to induce antibodies according to methods well known in the art. See, for instance, Sutcliffe et al., supra; Wilson et al., supra; Chow et al., Proc. Natl. Acad. Sci. USA 82:910-914; and Bittle et al., J. Gen. Virol. 66:2347-2354, 1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al. (1984), supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 discloses linear $C_{1-7}$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric IBABP-L protein or protein fragment alone (Fountoulakis et al., J. Biochem. 270:3958-3964 (1995)).

Diagnostic Methods

The present invention provides methods for detecting the presence of IBABP-L polynucleotides (for example, IBABP-L mRNA) or polypeptides in a sample, such as a biological sample from an individual; for quantitating IBABP-L polynucleotides or polypeptides in a sample; for determining an IBABP-L/IBABP polynucleotide or polypeptide ratio in a sample, etc.

In the methods of the present invention, a measurement of IBABP-L polypeptide or polynucleotide or an IBABP-L/IBABP ratio is compared to a "reference." Depending on the embodiment of the invention, such a reference can include a measurement or ratio in a control sample; a standard value obtained by measurements of a population of individuals; a baseline value determined for the same individual at an earlier timepoint, e.g., before commencing a course of treatment; or any other suitable reference used for similar methods.

As used herein, the term "individual" or "patient" refers to a mammal, including, but not limited to, a mouse, rat, rabbit, cat, dog, monkey, ape, human, or other mammal.

By "biological sample" is intended any biological sample obtained from an individual, including but not limited to, a fecal (stool) sample, body fluid (e.g., blood), cell, tissue, tissue culture, or other source that contains IBABP-L protein or mRNA. Methods for obtaining stool samples, tissue biopsies and other biological samples from mammals are well known in the art.

Detection of mRNA.

Total cellular RNA can be isolated from a biological sample using any suitable technique such as the single-step guanidinium-thiocyanate-phenol-chloroform method described in Chomczynski and Sacchi, Anal. Biochem. 162: 156-159 (1987). Levels of mRNA encoding IBABP-L are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., Cell 63:303-312, 1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. IBABP-L cDNA labeled according to any appropriate method (such as a $^{32}$P-multiprimed DNA labeling system is used as probe. After hybridization overnight, the filter is washed and exposed to x-ray film. cDNA for use as probe according to the present invention is described in the sections above.

S1 mapping can be performed as described in Fujita et al., Cell 49:357-367, 1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding IBABP-L). Northern blot analysis can be performed as described above.

According to one embodiment, levels of mRNA encoding IBABP-L are assayed using a polynucleotide amplification method, including but not limited to a polymerase chain reaction (PCR). One PCR method that is useful in the practice of the present invention is the RT-PCR method described in Makino et al., Technique 2:295-301, 1990), for example. By this method, the radioactivity of the DNA products of the amplification, i.e., the "amplification products" or "amplicons," in the polyacrylamide gel bands is linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding IBABP-L is quantified using an imaging analyzer. RT and PCR reaction ingredients and conditions, reagent and gel concentrations, and labeling methods are well known in the art.

According to one embodiment of an amplification method of the invention, primers are employed that selectively amplify an IBABP-L polynucleotide in a sample, for example, a primer pair including at least one primer that selectively hybridizes to IBABP-L mRNA (e.g., that includes sequences from the region of the IBABP-L mRNA that encodes the IBABP-L N-terminal polypeptide. The second primer can include any sequence from the target IBABP-L polynucleotide, whether such a sequence is unique to IBABP-L or is shared by IBABP-L and IBABP. This embodiment is useful for amplifying only an IBABP-L transcript (mRNA) in a sample, for example.

According to another embodiment of the invention, primers are employed that selectively amplify an IBABP polynucleotide, for example, a primer pair that includes at least one primer that selectively hybridizes to IBABP mRNA (e.g., that includes sequences from exon 4a. The second primer can include any sequence from the target IBABP polynucleotide, whether such a sequence is unique to IBABP-L or is shared by IBABP-L and IBABP. This embodiment is useful for amplifying only an IBABP transcript (mRNA) in a sample, for example.

According to another embodiment of the invention, primers are employed that amplify both an IBABP-L polynucleotide and an IBABP polynucleotide. For example, two primer pairs (i.e., 4 primers) can be used, one pair that selectively amplifies IBABP-L and a second pair that selectively amplifies IBABP, so as to produce amplification products that can be distinguished from one another, for example by length. As one example for illustrative purposes, a four-primer amplification system could include: a primer pair for amplifying IBABP-L mRNA that includes (1) a 5' primer that includes a sequence from the region of the IBABP-L cDNA that encodes the 49 amino acid N-terminal 49 amino acid N-terminal polypeptide of IBABP-L; and (2) a 3' primer that includes a sequence from the IBABP-L cDNA that is 3' to the 5' primer; and a primer pair for amplifying IBABP mRNA that includes (3) a 5' primer that includes a sequence from exon 4a (which is unique to the IBABP cDNA); and (4) a 3' primer that includes a sequence 3' to exon 4a that is present on IBABP cDNA. Alternatively, a three-primer system can be used, one that hybridizes selectively to IBABP-L, one that hybridizes selectively to IBABP, and a third that hybrids selectively to both IBABP-L and IBABP (i.e., that includes a sequence shared by both IBABP-L and IBABP). As one example for illustrative purposes, a three-primer amplification system could include: (1) a 5' primer that includes a sequence from the region of the IBABP-L cDNA that encodes the N-terminal 49 amino acid sequence of IBABP-L polypeptide (which is unique to the IBABP-L cDNA); (2) a 5' primer that includes a sequence from exon 4a (which is unique to the IBABP cDNA); and (3) a 3' primer that includes a sequence 3' to exon 4a that is present on both the IBABP-L and IBABP cDNAs. This embodiment is useful, for example, for determining the ration of IBABP-L mRNA to IBABP mRNA in a sample.

The skilled artisan will be able to produce additional primers, primer pairs, and sets of primers for PCR and other amplification methods based on the sequences taught herein.

One embodiment of the present invention is a kit that includes primers useful for amplification methods according to the present invention. Such kits also include suitable packaging, instructions for use, or both.

Another PCR method useful for detecting the presence of and/or quantitating IBABP-L mRNA and protein in a biological sample such as a fecal (e.g., stool) sample, is through the use of "bio-barcode" nanoparticles. For detection and/or quantitation of proteins, for example, two types of capture particles are employed: one is a micro-size magnetic particle bearing an antibody selective for a target protein, and the other is a nanoparticle with attached antibodies selective for the same protein. The nanoparticle also carries a large number (e.g., ~100) of unique, covalently attached oligonucleotides that are bound by hybridization to complementary oligonucleotides. The latter are the "bio-barcodes" that serve as markers for a selected protein. Because the nanoparticle probe carries many oligonucleotides per bound protein, there is substantial amplification, relative to protein. There is a second amplification of signal in a silver enhancement step. The result is 5-6 orders of magnitude greater sensitivity for proteins than ELISA-based assays, by detecting tens to hundreds of molecules. See, e.g., U.S. Pat. No. 6,974,669. See also, e.g., Stoeva et al., J. Am. Chem. Soc. 128:8378-8379, 2006, for an example of detection of protein cancer markers with bio-barcoded nanoparticle probes. The bio-barcode method can also be used for detecting and/or quantitating mRNA and other polynucleotides in a sample (Huber et al., Nucl. Acids Res. 32:e137, 2004; Cheng et al., Curr. Opin. Chem. Biol. 10:11-19, 2006; Thaxton et al., Clin. Chim. Acta 363:120-126, 2006; U.S. Pat. No. 6,974,669).

Detection of Polypeptide.

Assaying the presence of, or quantitating, IBABP-L polypeptide in a biological sample can occur using any art-known method.

Antibody-based techniques are useful for detecting the presence of and/or quantitating IBABP-L levels in a biological sample. For example, IBABP-L expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of IBABP-L for Western-blot or dot/slot assay (Jalkanen et al., J. Cell. Biol. 101:976-985, 1985; Jalkanen et al., J. Cell. Biol. 105:3087-3096, 1987). In this technique, which is based on the use of cationic solid phases, quantitation of IBABP-L can be accomplished using isolated IBABP-L as a standard. This technique can also be applied to body fluids. With these samples, a molar concentration of IBABP-L will aid to set standard values of IBABP-L content for different tissues, fecal matter, body fluids (serum, plasma, urine, synovial fluid, spinal fluid), etc. The normal appearance of IBABP-L amounts can then be set using values from healthy individuals, which can be compared to those obtained from a test subject.

Other antibody-based methods useful for detecting IBABP-L levels include immunoassays, such as the enzyme linked immunosorbent assay (ELISA), the radioimmunoassay (RIA), and the "bio-barcode" assays described above. For example, IBABP-L-selective monoclonal antibodies can be used both as an immunoadsorbent and as an enzyme-labeled probe to detect and quantify the IBABP-L. The amount of IBABP-L present in the sample can be calculated by reference to the amount present in a standard preparation using a linear regression computer algorithm. Such an ELISA for detecting a tumor antigen is described in Iacobelli et al., Breast Cancer Research and Treatment 11:19-30, 1988. In another ELISA assay, two distinct selective monoclonal antibodies can be used to detect IBABP-L in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting IBABP-L with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase, for example, has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^3$H), indium ($^{112}$In), and technetium ($^{99}$Tc), and fluorescent labels, such as fluorescein and rhodamine, and biotin.

In addition to assaying IBABP-L levels in a biological sample obtained from an individual, IBABP-L can also be detected in vivo by imaging. Antibody labels or markers for in vivo imaging of IBABP-L include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

An IBABP-L-selective antibody or antibody fragment which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain IBABP-L. In vivo tumor imaging is described in Burchiel et al., "Immunopharmacokinetics of Radiolabeled Antibodies and Their Fragments" (Chapter 13 in Tumor Imaging: The Radiochemical Detection of Cancer, Burchiel and Rhodes, eds., Masson Publishing Inc., 1982).

IBABP-L-selective antibodies for use in the present invention can be raised against the intact IBABP-L or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (or "fragment antibodies") (such as, for example, Fab and F(ab').sub.2 fragments) which are capable of selectively binding to IBABP-L. Fab and F(ab').sub.2 fragments lack the Fc portion of intact antibody, clear more rapidly from the circulation, and may have less non-specific tissue binding of an intact antibody (Wahl et al., J. Nucl. Med. 24:316-325, 1983).

The antibodies of the present invention may be prepared by any of a variety of methods. For example, cells expressing the IBABP-L or an antigenic fragment thereof can be administered to an animal in order to induce the production of sera containing polyclonal antibodies. In one method, a preparation of IBABP-L protein is prepared and purified as described above to render it substantially free of natural contaminants. Such a preparation is then introduced into an animal in order to produce polyclonal antisera of greater specific activity.

The antibodies of the present invention include monoclonal antibodies (or IBABP-L binding fragments thereof). Such monoclonal antibodies can be prepared using hybridoma technology (Colligan, Current Protocols in Immunology, Wiley Interscience, New York (1990-1996); Harlow & Lane, Antibodies: A Laboratory Manual, Cold Spring Harbor Press, Cold Spring Harbor, N.Y. (1988), Chapters 6-9, Current Protocols in Molecular Biology, Ausubel, infra, Chapter 11). In general, such procedures involve immunizing an animal (for example, a mouse or rabbit) with an IBABP-L antigen or with an IBABP-L-expressing cell. Suitable cells can be recognized by their capacity to bind anti-IBABP-L antibody. Such cells may be cultured in any suitable tissue culture medium, such as Earle's modified Eagle's medium supplemented with 10% fetal bovine serum (inactivated at about 56° C.), and supplemented with about 10 µg/1 of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al., Gastroenterology 80:225-232, 1981); Harlow & Lane, infra, Chapter 7. The hybridoma cells obtained through such a selection are then assayed to identify clones which secrete antibodies capable of binding the IBABP-L antigen.

Alternatively, additional antibodies capable of binding to the IBABP-L antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, IBABP-L-selective antibodies are used to immunize an animal, such as a mouse. The splenocytes of such an animal are then used to produce hybridoma cells, and the hybridoma cells are screened to identify clones which produce an antibody whose ability to bind to the IBABP-L-selective antibody can be blocked by the IBABP-L antigen. Such antibodies comprise anti-idiotypic antibodies to the IBABP-L-selective antibody and can be used to immunize an animal to induce formation of further IBABP-L-selective antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, IBABP-L-binding fragments can be produced through recombinant DNA technology or protein synthesis.

Where in vivo imaging is used to detect enhanced levels of IBABP-L for diagnosis in humans, one may use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, Science 229:1202, 1985; Oi et al., BioTechniques 4:214, 1986; Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643, 1984; Neuberger et al., Nature 314:268, 1985.

Further suitable labels for the IBABP-L-selective antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{09}$Pd, etc. $^{111}$In has advantages where in vivo imaging is used since its avoids the problem of dehalogenation of the $^{125}$I- or $^{131}$I-labeled monoclonal antibody by the liver. In addition, this radionucleotide has a more favorable gamma emission energy for imaging (Perkins et al., Eur. J. Nucl. Med. 10:296-301, 1985); Carasquillo et al., J. Nucl. Med. 28:281-287, 1987). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870, 1987).

Examples of suitable non-radioactive isotopic labels include $^{157}$Gd, $^{55}$Mn, $^{162}$Dy, $^{52}$Tr, and $^{56}$Fe.

Examples of suitable fluorescent labels include $^{152}$Eu label, fluorescein, isothiocyanate, rhodamine, phycoerythrin, phycocyanin, allophycocyanin, o-phthaldehyde, and fluorescamine.

Examples of suitable toxin labels include diphtheria toxin, ricin, and cholera toxin. Examples of chemiluminescent labels include luminal, isoluminal, aromatic acridinium ester, imidazole, acridinium salt, oxalate ester, luciferin, luciferase, and aequorin.

Examples of nuclear magnetic resonance contrasting agents include heavy metal nuclei such as Gd, Mn, and Fe.

Typical techniques for binding the above-described labels to antibodies are provided by Kennedy et al. (Clin. Chim.

Acta 70:1-31, 1976), and Schurs et al. (Clin. Chim. Acta 81:1-40, 1977). Coupling techniques mentioned in the latter are the glutaraldehyde method, the periodate method, the dimaleimide method, the m-maleimidobenzyl-N-hydroxy-succinimide ester method.

One use for diagnostic compositions and methods of the present invention is for the detection of the presence of colorectal cancer (or another condition marked by the up-regulation and/or increased expression of IBABP-L) in a patient or to identify individuals at increased risk of developing colorectal cancer. Another use is to identify patients who are more likely to be responsive to a therapy, or to monitor the efficacy of therapy, directed toward colorectal cancer. Such therapies include frontline therapy with 5-FU/FA in combination with irinotecan and oxaliplatin or other therapies. The diagnostic compositions and method of the present invention are also useful for determining the efficacy of therapeutic agents for treatment and prophylaxis of colorectal cancer, including, but not limited to, agents that inhibit kinases, growth factor inhibitors, NF-κB inhibitors, bile acid replacement therapy, antibody therapy, radiation therapy, and combinations thereof. Various other uses, such as in research and clinical settings will be apparent to the skilled practitioner.

In methods in which is made a measurement of IBABP-L polynucleotide or polypeptide in a sample, or the IBABP-L/IBABP polynucleotide or polypeptide ratio in a sample, the measurement can be compared to a reference, e.g., a similar measurement from a control sample from the individual, a measurement from the individual taken at one or more different timepoints (e.g., a baseline measurement before commencing therapy or a measurement at one or more timepoints during and/or after a course of therapy); a value derived from measurements taken from a population of individuals who are healthy, suffer from various stages of colorectal cancer, are at enhanced risk of developing colorectal cancer, etc.; and other such reference values.

Therapeutic and Prophylactic Administration of IBABP-L Polypeptide

IBABP-L polypeptides of the present invention may be useful in treating patients at risk for, or suffering from, colorectal cancer or other cancers. As noted in Example 1, IBABP-L may serve as a defense mechanism against secondary bile acid-mediated apoptosis. Increased levels of IBABP-L would allow more binding of bile acids, sequestering bile acids extracellularly, decreasing cellular bile acid concentration and thus lessen contact with carcinogens, and providing a protective buffer against bile acid damage. As a result, patients, including but not limited to those having a genetic predisposition toward colorectal cancer or who have been treated for colorectal cancer and for whom recurrence is a threat, may be treated with IBABP-L in order to lessen the likelihood of a colorectal cancer (or its recurrence). Thus, the IBABP-L can be exogenously added to cells, tissues, or the body of an individual to produce a therapeutic effect.

One of ordinary skill will appreciate that effective amounts of a IBABP-L polypeptide can be determined empirically for each condition where administration of a such a polypeptide is indicated. The polypeptide having IBABP-L activity can be administered in pharmaceutical compositions in combination with one or more pharmaceutically acceptable carriers, diluents and/or excipients. As one example for illustrative purposes only, IBABP-L polypeptide can be administered in a capsule or pill having an enteric coating for release in the lower gastrointestinal tract. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

The IBABP-L composition to be used in the therapy will also be formulated and dosed in a fashion consistent with good medical practice, taking into account the clinical condition of the individual patient (especially the side effects of treatment with IBABP-L alone), the site of delivery of the IBABP-L composition, the method of administration, the scheduling of administration, and other factors known to practitioners.

An effective amount of an IBABP-L polypeptide (or a composition comprising an IBABP-L polypeptide) for purposes herein is thus determined by such considerations. As used herein, "effective amount" refers to an amount of a composition that causes a detectable difference in an observable biological effect, including but not limited to, a statistically significant difference in such an effect. The detectable difference may result from a single substance in the composition, from a combination of substances in the composition, or from the combined effects of administration of more than one composition. For example, an "effective amount" of a composition comprising an IBABP-L polypeptide may refer to an amount of the composition that kills a cancer cell, treats or prevents cancer or another disease or disorder, or treats the symptoms of cancer or another disease or disorder, in an individual. A combination of an IBABP-L polypeptide and another substance, e.g., an anti-cancer agent, or other active ingredient, in a given composition or treatment may be a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, "treating" or "treat" includes (i) preventing or delaying a pathologic condition from occurring (e.g. prophylaxis); (ii) inhibiting the pathologic condition or arresting its development or progression; (iii) relieving the pathologic condition; and/or reducing the severity or duration of one or more symptoms associated with the pathologic condition; or any other clinically relevant measure of efficacy.

The length of treatment needed to observe changes and the interval following treatment for responses to occur appears to vary depending on the desired effect.

One embodiment of a pharmaceutical composition of the invention is a pill or capsule suitable for delivery of IBABP-L polypeptide to the gut of a patient, including but not limited to the colon or rectum.

The IBABP-L polypeptide may be administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release IBABP-L compositions also include a liposomally entrapped IBABP-L polypeptide. Liposomes containing a IBABP-L polypeptide are prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal IBABP-L therapy.

For parenteral administration, in one embodiment, the IBABP-L polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, according to one embodiment of the invention, the formulation does not include oxidizing agents and other compounds that are known to be deleterious to polypeptides.

The formulations may be prepared by contacting the IBABP-L polypeptide uniformly and intimately with liquid carriers or finely divided solid carriers or both. Then, if necessary, the product is shaped into the desired formulation. If the carrier is a parenteral carrier, or a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

It will be understood that the use of certain of the foregoing excipients, carriers, or stabilizers will result in the formation of IBABP-L salts.

IBABP-L to be used for therapeutic administration must be sterile. Sterility is readily accomplished by filtration through sterile filtration membranes (e.g., 0.2 micron membranes). Therapeutic IBABP-L compositions generally are placed into a container having a sterile access port, for example, an intravenous solution bag or vial having a stopper pierceable by a hypodermic injection needle.

IBABP-L may be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IBABP-L solution, and the resulting mixture is lyophilized. The infusion solution is prepared by reconstituting the lyophilized IBABP-L using bacteriostatic Water-for-Injection.

The invention will be better understood by reference to the following Examples, which are intended to merely illustrate the best mode now known for practicing the invention. The scope of the invention is not to be considered limited thereto.

Example 1

We have discovered that IBABP is useful as a biomarker for colorectal cancer. Recent work indicated up-regulation in the expression of IBABP in colorectal tumors (DeGottardi et al., Dig. Dis. Sci. 49:982-989, 2004). However, our in-depth analysis of the gene structure of IBABP surprisingly reveals a new variant of IBABP that we call IBABP-L. IBABP-L arises from an alternative start site in the IBABP gene and consequently encodes the 49-residue N-terminal sequence of IBABP-L. Most significantly, IBABP-L is up-regulated in all stages of colorectal cancer and in malignant colon polyps. We also show that the up-regulation of IBABP reported in a prior study (DeGottardi et al., Dig. Dis. Sci. 49:982-989, 2004) can be attributed entirely to up-regulation of IBABP-L; the expression of the shorter transcript encoding the 14 kDa IBABP is not significantly changed in colorectal cancer.

Materials and Methods

Cell Lines and Tissue Samples.

Human colorectal cancer cell lines (Caco-2, SW480, HCT116, LS 174T, LoVo, SW403, WiDr, and HT-29, obtained from the American Type Culture Collection (Manassas, Va.) were grown in Dulbecco's modified Eagle's media (DMEM; Irvine Scientific, Santa Ana, Calif.) containing 1 mM sodium pyruvate, 4.5 g/L D-glucose, 4 mM L-glutamine, and supplemented with 10% fetal bovine serum (Irvine Scientific), and 100 U/ml penicillin, 100 µg/ml streptomycin and 0.25 µg/ml amphotericin B (Omega Scientific, Tarzana, Calif.). Cells were maintained in 100 mm standard cell culture dishes (Falcon, BD Biosciences, San Jose, Calif.) and grown at 37° C. under 5% $CO_2$.

Matched human colorectal carcinoma and adjacent normal mucosa were purchased from Asterand, Inc. (Detroit, Mich.), or obtained from the Cooperative Human Tissue Network (service of the National Cancer Institute, Bethesda, Md.); patients have provided written consent for use of tissues for scientific purpose. In total, 68 matched human colorectal carcinoma samples were examined (52.9% male donor, 86.8% Caucasian). Patient ages range from 21 to 89 years (76.5% greater than 50 years old). Colorectal carcinomas were distributed by intestinal region as follows: cecum, 11.3%; colon, 48.3%; and rectum, 40.3%; by histological typing: well-differentiated, 27.1%; moderately differentiated, 61.0%; and poorly differentiated, 11.9%; and by clinical stage: stage I, 11; stage II, 20; stage III, 17; stage IV, 15; unclassifiable, 5 (not specified in pathology reports provided). Eleven polyp samples were also examined, five of which contained focal high grade dysplasia, one case from the familial adenomatous polyposis (FAP) family, and one case of inherited juvenile polyposis syndrome.

Assessing the Expression of IBABP by PCR.

Expression of mRNA encoding IBABP-L (Genbank accession number DQ132786) and IBABP (Genbank accession number NM_001445) along the digestive tract was measured with RNA from normal human intestine and liver purchased from Invitrogen and from Biochain Institute, Inc. (Hayward, Calif.) by quantitative RT-PCR. Expression of ARPP0 was used as a control. The expression of IBABP and IBABP-L in human tumor and adjacent normal tissue was measured with tissues purchased from Asterand, Inc. (Detroit, Mich.), and the Cooperative Human Tissue Network as described above.

Total RNA was isolated from tissues using TRIZOL reagent (Invitrogen, Carlsbad, Calif.) in a protocol combined with the RNeasy Mini Kit (Qiagen Inc., Valencia, Calif.). For each sample, frozen tissue (approximately 0.1 g) was cut and soaked in pre-chilled RNAlater-ICE stabilizing solution (1.0 ml; Ambion Inc., Austin, Tex.) for 24 h at −20° C. Tissue was minced using a surgical scalpel, immersed in TRIZOL (1.0 ml), and homogenized using a Tissue-Tearor (BioSpec Products, Inc., Bartlesville, Okla.). Chloroform (200 µl) was added to homogenized tissue and sample was mixed by vortexing for 30 s. Samples were centrifuged (12,000×g, 10 minutes at 4° C.) to separate phases. The aqueous phase was removed, added to an equal volume of 70% ethanol, mixed by pipetting, and loaded into the RNeasy column. Following RNA binding, an on-column DNase digestion protocol using RNase-Free DNase Set (Qiagen) was performed according to manufacturer instructions.

To determine the relative expression levels of IBABP-L and IBABP, a two-step quantitative RT-PCR procedure was used. In the first step, complementary DNA (cDNA) was synthesized from total RNA. For each sample, RNA (2.0 µg) was reversed transcribed using SuperScript First-Strand Synthesis System for RT-PCR (Invitrogen) in a 20 µl final reaction volume containing: 10 mM dNTP mix (1.0 µl), 0.5 µg/ml Oligo(dT)$_{12-18}$ (1.0 µl), 0.1 M DTT (2.0 µl), 25 mM MgCl2 (4.0 µl), 10× RT buffer (2.0 µl), RNaseOUT Recombinant RNase Inhibitor (1.0 µl), and SuperScript II Reverse Transcriptase (1.0 µl). Reverse transcription was performed at 42° C. for 50 min and terminated by heating to 70° C. for 15 minutes followed by chilling samples on ice. Template RNA was cleaved by incubating with RNase H (1.0 µl) for 20 min at 37° C. In the second step, quantitative PCT (QPCR) was carried out on a Mx 3000P Real-Time PCR System (Stratagene, La Jolla, Calif.) using a solution containing diluted cDNA (1:20; 2.0 µl), 1×SYBR Green PCR Master Mix (Applied Biosystems, Foster City, Calif.), and primers for IBABP-L, IBABP, or ARPP0 (0.25 µM). The primer sets are IBABP: 5' CCACCCATTCTCCTCATCCCTCTGCTC 3' (in exon 4a) (SEQ ID NO: 10), 5' ACCAAGTGAAGTCCTGCCCATCCTG 3' (in exon 5) (SEQ ID NO: 11); IBABP-L: 5' ACATGGGTGAGCCGGAAAGGAGAC 3' (in exon 3) (SEQ ID NO: 12), 5' CCGGAGTAGTGCTGGGACCAAGTGAAGT 3' (in exon 5) (SEQ ID NO: 13); ARPP0: 5' CAAGACTGGAGACAAAGTGG 3' (SEQ ID NO: 14), 5' AATCTGCAGACAGACACTGG 3' (SEQ ID NO: 15). All primers were designed using PrimerSelet™ (DNASTAR, Inc., Madison, Wis.) and synthesized by Integrated DNA Technologies, Inc. (Coralville, Iowa). The following cycling parameters were used: denaturation at 95° C. for 15 s, annealing at 56° C. for 20 s, extension at 72° C. for 30 s, and detection at 78° C. for 5 s. After 40 cycles, PCR products were subjected to dissociation curve analysis to check the PCR specificity. Values obtained from QPCR were normalized to expression of ARPP0.

Regulation of Expression of the IBABP Variants in Caco-2 Cells.

Caco-2 cells were seeded in six-well plates (Falcon) at 2×10⁵ cells/well. Medium was exchanged every two days until cells reached 100% confluence and began spontaneous differentiation. Stock solutions of CDCA and DCA (Sigma-Aldrich Co., St. Louis, Mo.), as free acids, were prepared in absolute ethanol (100 mM) and stored at −20° C. A stock solution of 9-cis-retinoic acid (9cRA; Sigma-Aldrich) was dissolved in dimethyl sulfoxide (DMSO; 100 µM) and stored at −20° C. Confluent Caco-2 cells were incubated at 37° C. for 24 h in medium containing CDCA or DCA (100 µM), 9cRA (100 nM), or DMEM only (0.1% solvent concentration). Cells were harvested, cellular RNA was isolated using the RNeasy Mini Kit (Qiagen) according to manufacturer instruction, and expression of IBABP variants was determined by QPCR as described above.

Generation of Antibodies to IBABP-L and Immunohistochemical Studies.

A peptide with sequence CTWVSRKGDLQRMKQTHKGKPPSS, which is present in the 49-residue N-terminal sequence of IBABP-L, was synthesized, conjugated to keyhole limpet hemocyanin (KLH), and used as an antigen to immunize rabbits. The antisera from immunized animals were tested for reactivity against recombinant IBABP-L and IBABP by Western blot. Recombinant IBABP-L and IBABP were expressed and purified using pGEX system. Recombinant proteins were expressed as fusion proteins with a Histidine-Tag, which was removed by digestion with thrombin while the protein was bound to a nickel resin. After digestion thrombin was removed with benzamidine-Sepharose.

Paraffin-embedded slides were stained with anti IBABP-L antiserum (1:2000) and followed by a diaminobenzidine-based detection method employing horseradish peroxidase system. The slides were then counterstained with hematoxylin.

Data Analysis and Statistics.

The change in RNA expression of IBABP-L and IBABP between diseased colon tissue and matched adjacent normal mucosa was analyzed using two strategies. In the first, expression level of the variant in cancer or polyp tissue to that of its adjacent normal mucosa resulted in a fold of change value for each variant. Using a two-fold cut-off limit, a value of 2.0 or greater denoted up-regulation, whereas a value of less than 0.5 denoted down-regulation. In the second method, we calculated the ratio of IBABP-L to IBABP in cancer or polyp tissue ($R_C$ and $R_P$) and in adjacent normal mucosa ($R_N$). Again using a two-fold cut-off, a ratio greater than or equal to 2.0 denoted up-regulation of IBABP-L in cancer or polyp; a value of less than 0.5 denotes down-regulation. The value from both strategies was grouped according to the parameters of clinical specimen (gender, age, race, tumor size, tumor locale, differentiation level, and clinical stage) and correlation between expression level and clinical parameters was analyzed by t-test and one way ANOVA.

Results

Characterization of the Gene Encoding IBABP-L.

A BLASTN search of the NCBI human expression sequence tag (EST) database (http://www.ncbi.nlm.nih.gov/) using NM_001445 revealed two ESTs (BM974219 and BU683560) that was largely identical to IBABP, except that the newly discovered transcript encoded a protein having a 49-aa sequence at its N-terminus that is not present in IBABP. Since the transcript of this variant is longer than that of IBABP, we call it IBABP-L. The gene for IBABP-L (chromosome 5q33.3-q34; contig NT_023133) is identical to that of the known form, IBABP. However, the mRNA encoding IBABP-L contains seven exons, three of which are unique and are present at the 5' end of the gene. The shorter protein IBABP contains only four exons and its transcription is initiated within the third intron of the IBABP-L (fabp6) gene. FIG. 1 shows the structure of IBABP-L (also called fabp6).

Thus, the two variants of IBABP share exons 5 through 7. Transcripts encoding both variants are detected in human intestine. The presence of exons unique to IBABP-L permitted the design of variant-specific primers to distinguish expression of IBABP-L from IBABP. As described below, these primers were used to detect the expression of each variant in mRNA extracted from normal human intestine by RT-PCR.

The complete nucleotide sequence of the IBABP-L transcript was deposited in Genebank with accession number DQ132786.

FIG. 2 shows the open reading frame of the IBABP gene (i.e., genomic sequence), which encodes both IBABP-L and IBABP. In FIG. 2, the open reading frame of IBABP (the 14 kDa form) is underlined, with the additional open reading frame sequence for IBABP-L highlighted (grey). Thus, the open reading frame for IBABP-L contains much of the ORF for IBABP, but also an additional 627 nucleotides on the 5' end of the gene. FIG. 3 shows DNA sequences from the IBABP gene that are unique to IBABP-L (highlighted in gray in FIG. 2).

FIG. 4 shows an alignment of cDNA sequences for IBABP-L and IBABP. The cDNA sequence for IBABP-L (top line) is shown with the ATG start site noted in bold. The cDNA sequence for IBABP (bottom line) are highlighted in gray. Exons 1, 2 and 3 are unique to IBABP-L (note dashes showing a lack of any homologous exon for IBABP). Exon 4a (underlined) is present only in the cDNA for IBABP. Exons 4b-7 are shared by the cDNAs for both IBABP-L and IBABP.

FIG. 5 shows the cDNA sequence encoding IBABP-L, and FIG. 6 shows the nucleotide sequence encoding the N-terminal 49 amino acid sequence from the IBABP-L cDNA.

FIG. 7 shows an alignment of polypeptide sequences for IBABP-L (top line) and IBABP (bottom line, highlighted in gray). IBABP-L polypeptide contains a 49 amino acid sequence at its N-terminus that is absent from the IBABP polypeptide. FIG. 8 shows the predicted polypeptide sequence of IBABP-L. The 49 amino acid N-terminal sequence of IBABP-L that is not found in the IBABP polypeptide is highlighted in gray.

Expression Pattern of IBABP and IBABP-L in Gastrointestinal Tissue.

The IBABP gene is primarily expressed in the intestine. Therefore, we compared the expression of the transcripts encoding IBABP and IBABP-L in the gastrointestinal tract, particularly tissues associated with the enterohepatic bile acid cycle (human liver, gallbladder and intestinal sections). Oligonucleotides capable of selectively priming the amplification of each variant were used to initiate real-time Q-PCR reactions. The copy number of mRNA transcripts was normalized to the expression of the housekeeping gene acidic ribosomal phosphoprotein (ARPP0), also known as ribosomal protein large P0 (RPLP0), often used as an endogenous control in prostate and colon cancer research (Chene et al., Int. J. Cancer 111:798-804, 2004; Cacev et al., Gut 54:1129-1135, 2005). FIG. 9 shows expression of IBABP and IBABP-L in the gastrointestinal tract. The transcript encoding IBABP-L was found at similar levels in all tissues tested with the exception of the rectum where it was expressed at lower levels (FIG. 9). By contrast, the expression of IBABP is localized to a section of the intestine extending from the jejunum through ascending colon. In these sections, the expression of IBABP was ten to one thousand-fold higher than the expression of IBABP-L.

Bile Acids Differentially Regulate the Variants of IBABP.

Figure 10:
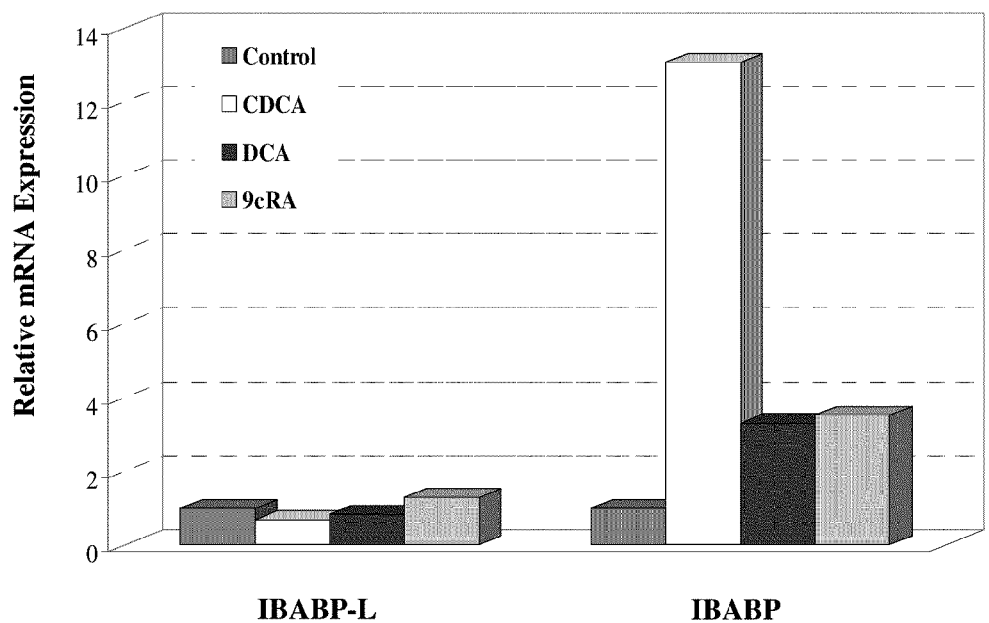
FIG. 10 shows that agonists of FXR and RXR regulate the expression of IBABP but not IBABP-L. Human Caco-2 (enterocyte-like) cells were incubated with FXR agonists chenodeoxycholic acid (CDCA) or deoxycholic acid (DCA) (100 µM) or with the RXR agonist 9cRA (100 nM) for 24 h. The expression of IBABP-L and IBABP was measured by quantitative RT-PCR. The mRNA copy number of each variant is normalized to the expression the housekeeping gene ARPP0. Values in the figure represent the average of three experiments with each replicate performed in duplicate.

Many of the genes involved in bile acid homeostasis are regulated through the FXR nuclear hormone receptor (Forman et al., Cell 81:687-693, 1995), which binds directly to bile acids (Makishima et al., Science 284:1362-1365, 1999; Parks et al., Science 284:1365-1368, 1999). In fact, the expression of IBABP is also regulated by the FXR (Kanda et al., Biochem. J. 330 (Pt. 1):261-265, 1998; Grober et al., J. Biol. Chem. 274:29749-29754, 1999). The effect of bile acids and 9-cis-retinoic acid, a ligand for RXR (the partner of FXR) on the expression of IBABP-L and IBABP was studied. Caco-2 cells were treated with either chenodeoxycholic acid (CDCA), deoxycholic acid (DCA), or 9cRA, and the relative expression of transcripts encoding IBABP-L and IBABP was measured by quantitative RT-PCR (FIG. 10). As expected, CDCA and DCA increased expression of IBABP up to 13-fold, but unexpectedly these agents were without effect on expression of IBABP-L. Similarly, 9cRA also elicited the up-regulated of IBABP, but was without effect on IBABP-L. These results are consistent with the idea that the two variants of IBABP arise from separate transcription start sites.

mRNA Encoding IBABP-L is Up-Regulated in Colorectal Cancer.

Figure 11:
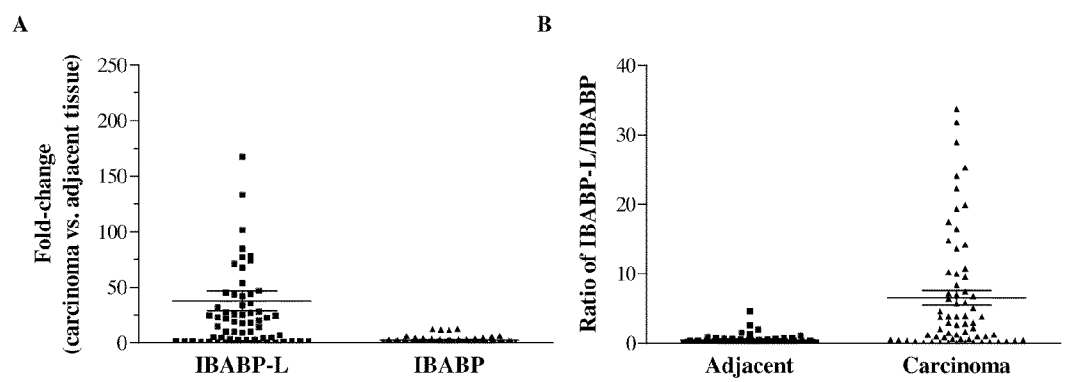
FIG. 11 shows up-regulation of IBABP-L in colorectal carcinoma. Total RNA was isolated from 68 sets of matched human colorectal and adjacent normal mucosa and used as template in a two-step quantitative RT-PCR procedure. Variant-specific primers were used to quantify mRNA encoding IBABP-L and IBABP. Values were normalized to expression of ARPP0. The expression difference between carcinoma and normal mucosa was expressed as fold change of IBABP variants between carcinoma and normal mucosa (A) or as the ratio of IBABP-L to IBABP in colorectal carcinoma ($R_C$) versus adjacent normal mucosa ($R_N$) (B). Error bars represent mean±SEM.

The expression of each variant of IBABP was measured in various stages of colon cancer by quantitative RT-PCR using IBABP or IBABP-L selective primer sets. In all cases the level of the transcript in carcinoma was compared to its levels in adjacent normal tissue. The transcript encoding IBABP-L was substantially up-regulated in colon carcinoma; in some cases it was expressed at levels more than 100-fold higher than in normal tissue (FIG. 11A). IBABP-L was up-regulated in 76% ($^{52}/_{68}$) of colorectal cancers using two-fold cut-off ($P<0.0001$). In contrast, there was no significant change in the expression of IBABP in carcinoma tissue.

As an additional strategy to normalize for patient to patient variation in the expression levels of IBABP and IBABP-L, we compared their ratio of expression in colon cancer. In this instance the ratio of IBABP-L/IBABP in colorectal cancer ($R_C$) was compared to the ratio of expression in adjacent normal tissue ($R_N$) (FIG. 11B). In colorectal cancers $R_C$ differed significantly from adjacent normal tissue $R_N$ ($P<0.0001$). Using two-fold cut-off, the $R_C/R_N$ ratio increases in 78% ($^{53}/_{68}$) of colorectal cancers, indicating this measurement is a better predictive tool for identifying malignant tissue.

The IBABP-L Protein is Expressed and Up-Regulated in Colorectal Cancer.

Studies were conducted to determine if the IBABP-L protein is expressed in colon tissue or in colon cancer. First, antiserum against IBABP-L was raised in rabbits by immunization with the peptide CTWVSRKGDLQRMKQTHKGKPPSS (SEQ ID NO: 16), a peptide within the 40-residue N-terminal sequence found in IBABP-L. The antiserum from immunized animals was tested for reactivity against recombinant IBABP-L and IBABP by Western blot. Recombinant IBABP-L and IBABP were separated on SDS-PAGE, transferred to nitrocellulose and probed with the antiserum (1:2000 dilution). The Western blot was probed with antiserum against IBABP-L peptide or with antiserum raised against recombinant IBABP. The specificity of the anti-serum against IBABP-L was confirmed by competition with soluble peptide antigen. In this case, 2 µl of antisera was incubated with either 1 or 10 µg of antigen prior to use in Western blot. The antiserum was found to be highly specific for IBABP-L and without binding to IBABP. Furthermore, binding of the antiserum to IBABP-L could be blocked by competition with soluble peptide antigen.

The expression of IBABP-L protein was also measured in human colorectal carcinoma by immunohistochemistry using an IBABP-L selective antiserum. Paraffin-embedded slides of human colorectal carcinoma and its adjacent normal tissue were stained by rabbit antiserum raised against an IBABP-L selective peptide, followed by a diaminobenzidine-based detection method employing horseradish peroxidase system. Human fetal colon slide (Biochain) and normal adult ileum (Biospring) was also stained the same way. In some cases epithelial cells at the apex of the villi show weak staining for IBABP-L. However, the vast majority of epithelial cells in villi and crypts lack staining. In contrast, nearly all cancer cells were stained positively. The staining appeared to be independent of the differentiation status of the tumor. Interestingly, fetal ileum was also stained by antiserum against IBABP-L. Fetal epithelial cells all expressed IBABP-L, but this expression was lost in most adult epithelial cells. Importantly, adult ileum lacks expression of IBABP-L. This finding in contrast to the fact that IBABP is expressed to high levels in the ileum (Fujita et al., Eur. J. Biochem. 233:406-413, 1995; Grober et al., J. Biol. Chem. 274:29749-29754, 1999).

Effects of Tumor Stage on the Expression of IBABP-L and the Ratio of IBABP-L/IBABP.

Figure 12:
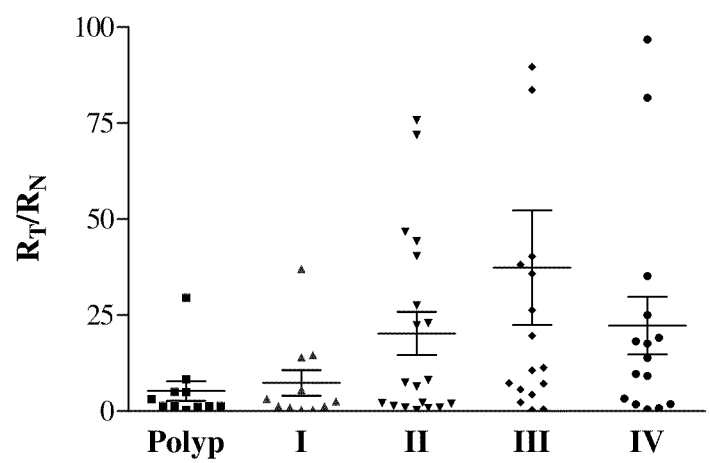
FIG. 12 shows the effect of clinical stage on up-regulation of IBABP-L The ratio of change for polyp to normal tissue ($R_P/R_N$) and tumor to normal tissue ($R_C/R_N$), collectively $R_T/R_N$ was separated by clinical stage. Bars represent mean±SEM. Difference between $R_P/R_N$ and $R_C/R_N$ from Stage II-IV carcinoma is significant ($P<0.02$).

Experiments were also conducted to determine if tumor stage significantly affects the expression of IBABP-L. We found an obvious trend toward increased expression of the mRNA encoding IBABP-L as a function of tumor stage, however this trend was not entirely statistically significant. Therefore, we explored whether patient-to-patient variance in IBABP-L could be normalized by dividing by the level of IBABP expression. The ratio of IBABP-L/IBABP was calculated for tumor tissue ($R_T$) and for normal adjacent tissue ($R_N$). As illustrated in FIG. 12, there is a trend of increasing $R_T/R_N$ across the first four stages of colon cancer (polyps to stage III). Although the differences are not significant between polyps and stage I, nor from stage II to stage IV, the difference between these two groups is statistically significant. The ratio of IBABP-L/IBABP in cancers was also independent of patient age, gender, differentiation level, and tumor locale.

IBABP-L is Expressed in Colon Carcinoma Cells Lines that Contain Distinct Oncogenic Lesions.

It is now clear that colorectal cancer can be initiated by a number of genetic lesions including the mutations and deletions in the tumor suppressor genes DCC, APC and p53 along with mutations in the oncogene K-ras. Experiments were conducted with colon cancer cell lines to determine if the type of oncogenic lesions influenced the ratio of expression between IBABP-L and IBABP. These studies were performed in colon cancer cell lines which contain distinct lesions (Table 1 below). The ratio of IBABP-L/IBABP in seven cell lines is more than 2.0 (from 2.17 to 19.65), only SW480 has a ratio less than 2.0 (1.42). Consequently, the type of oncogenic lesion has little effect on the ratio of IBABP-L to IBABP. These observations indicate that an assessment of the expression of IBABP-L is likely to be applicable in the detection of colon cancers arising from a broad range of oncogenic lesions.

Discussion

We have identified a new variant of IBABP and designated it as IBABP-L. The transcript for IBABP-L arises from an alternative start site and includes three exons that are absent in IBABP. IBABP-L also shares part of a fourth exon with IBABP. The protein encoded by IBABP-L contains a deduced 49 residue N-terminal sequence that is not found in IBABP. The IBABP-L transcript is expressed at similar levels throughout the normal human intestine. This is in contrast to the transcript encoding IBABP, which is expressed at levels several orders of magnitude higher in the section of the intestine extending from the jejunum to the ascending colon. In these regions of the intestine, the expression of IBABP-L is at least an order of magnitude lower than IBABP. The two transcripts also differ in their response to bile acids. While bile acids stimulate the expression of IBABP as part of the FXR transcription pathway (Grober et al., J. Biol. Chem. 274:29749-29754, 1999), they are without effect on the expression of IBABP-L.

IBABP was recently reported to be up-regulated in colorectal cancer in conjunction with a decrease in the expression of FXR (DeGottardi et al., Dig. Dis. Sci. 49:982-989, 2004). However, that study was performed prior to our discovery of IBABP-L, and did not distinguish between the two forms of IBABP. Here, we compared the expression of IBABP and IBABP-L in colorectal carcinoma samples from 68 patients. We report that IBABP remains essentially unchanged in colorectal cancer, but that its alternative transcript, IBABP-L, is up-regulated. In most cases the up-regulation is substantial, with the mean increase in relative mRNA copy number being greater than 30-fold. IBABP-L is up-regulated in early malignant polyps and its high expression is evident in all subsequent clinical classifications of tumor differentiation. Although a trend toward up-regulation in colorectal cancer is evident with PCR primers that fail to distinguish between the two transcripts, a specific measure of IBABP-L is far more sensitive.

Three other factors are important to consider in the use of IBABP-L as a potential biomarker. First, the increase in IBABP-L expression in colorectal cancer is independent of the patients' age or gender. Second, based on studies in colon cancer cells lines, the expression of IBABP-L appears to be independent of common oncogenic mutations to proteins like p53, APC, or K-ras. Any subtle links between IBABP-L and these oncogenic mutations will be best studied in larger more comprehensive analysis of tumor samples from patients. Nevertheless, in conjunction with the fact that IBABP-L is up-regulated in most tumors, the studies from cell lines show that it is highly unlikely that the expression of IBABP-L is dependent on a lesion in a single oncogene. Third, unlike IBABP, the expression of IBABP-L is not influenced by bile acids. Therefore, one would not expect the levels of IBABP-L to be tied to changes in bile acids resulting from dietary changes or overall health status. Collectively, the expression of IBABP-L has many properties that make it well suited for use as a broadly applicable test for colorectal cancer.

As with most studies comparing biomarker levels across populations of patients we used a normalization procedure. In this study we chose to use acidic ribosomal phosphoprotein (ARPP0) as a normalization standard because it is rather widely accepted for normalization in studies of gene expression in cancer (Chene et al., Int. J. Cancer 111:798-804, 2004; Cacev et al., Gut 54:1129-1135, 2005), and because our preliminary analysis indicated that this gene had the most consistent expression levels in colorectal tumors. However, there are other "housekeeping" genes that could be used for normalizing the expression levels of IBABP-L. We have conducted a small survey of tumor samples to gauge the applicability of other normalization standards, like Cyclophilin A, GADPH, and β-actin. Interestingly, when β-actin was used for normalization of IBABP-L, the assay detected tumors that were missed when ARPP0 was used. In fact, in sixteen tumors where the change in IBABP-L normalized to ARPP0 was less than two-fold, nine showed greater than a two-fold increase in IBABP-L when normalized to β-actin. We chose not to use β-actin as a normalization standard in the analysis of all sixty-eight tumors because β-actin levels are reported to change in colon cancer (Khimani et al., Biotechniques 38:739-745, 2005). While the observations on normalizing to β-actin have little impact on the overall conclusions of this report, they do suggest that the sensitivity of detecting colorectal cancer with IBABP-L could potentially increase through exploration of other genes for normalization. Such comparisons will await results from a larger clinical trial on IBABP-L as a biomarker. As another approach toward normalization we also calculated the ratio of expression between IBABP-L and IBABP ($R_C/R_N$) in samples, and we found this ratio to be a slightly better predictor of colorectal cancer than the relative levels of IBABP-L alone. The benefit of using $R_C/R_N$ instead of IBABP-L alone as a colorectal cancer biomarker and the biology behind this need to be further investigated.

The expression of IBABP-L, and its up-regulation in colon cancer are likely to impact our understanding of the role of secondary bile acids in the onset and progression of colon cancer. Although insufficient to initiate oncogenesis alone, secondary bile acids strongly promote tumorigenesis (Bernstein et al., Mutat. Res. 589:47-65, 2005). IBABP-L may be initially up-regulated as a defense mechanism against secondary bile acid-mediated apoptosis. Increased levels of IBABP-L would allow more binding of bile acids, decreasing cellular bile acid concentration and thus lessen contact with carcinogens. A protective buffer from bile acid damage may at first create a cellular growth advantage. However, an oncogenic program of uncontrolled cell growth: progression from hyperplasia to a final invasive phenotype, may later supplant any original benefit. The mechanism of this action remains unclear, however, raising the possibility that up-regulation of IBABP-L ultimately indicates participation as a signaling molecule in an as-yet-unknown pro-oncogenic pathway.

In summary, we observed significant differences in the transcription of IBABP-L between normal colon tissue and colon cancer. Statistically significant differences in the expression of IBABP-L are evident in all stages of colon cancer, ranging from polyps to Stage IV colorectal cancer. Therefore, IBABP-L is an especially exciting biomarker for colon cancer.

All publications, patents and patent applications are incorporated herein by reference. While in the foregoing specification, this invention has been described in relation to certain embodiments thereof, and many details have been set forth for purposes of illustration, it will be apparent to those skilled in the art that the invention is susceptible to additional embodiments and that certain of the details herein may be varied considerably without departing from the basic principles of the invention.

TABLE 1

Genetic lesions in colorectal cancer cell lines

|  | APC | TP53 | K-ras | Stage | Duke's type | IBABP-L/IBABP |
|---|---|---|---|---|---|---|
| Caco-2 | mutant | mutant | mutant | II | B | 2.17 ± 0.07 |
| SW480 | mutant | mutant | mutant | n/a* | B | 1.42 ± 0.07 |
| HCT116 | wild type | wild type | mutant | n/a* | n/a* | 15.10 ± 2.40 |
| LS 174T | wild type | wild type | mutant | n/a* | B | 19.65 ± 1.65 |
| LoVo | mutant | wild type | mutant | IV | C | 6.07 ± 0.66 |
| SW403 | mutant | wild type | mutant | III | C | 13.25 ± 0.65 |
| WiDr[#] | n/a* | mutant | wild type | n/a* | n/a* | 10.5 ± 0.20 |
| HT-29 | mutant | mutant | wild type | I | n/a* | 3.47 ± 0.34 |

[#]DNA fingerprinting has shown this line to be a derivative of HT-29.
*Not available from literature.

What is claimed is:

1. A method of determining a ratio of IBABP-L polynucleotide to IBABP polynucleotide in a sample that comprises IBABP-L polynucleotide and IBABP polynucleotide, the method comprising (a) contacting the sample with a first probe that hybridizes selectively to IBABP-L polynucleotide; (b) measuring hybridization of the first probe to the IBABP-L polynucleotide in the sample, (c) contacting the sample with a second probe that hybridizes selectively to IBABP polynucleotide and IBABP-L polynucleotide; (d) measuring the hybridization of the second probe to the IBABP polynucleotide and the IBABP-L polynucleotide in the sample; and (e) calculating the ratio of IBABP-L polynucleotide to IBABP polynucleotide in the sample.

2. The method of claim 1 wherein the IBABP-L polynucleotide is an mRNA.

3. The method of claim 1 comprising (a) contacting the sample with at least one primer that hybridizes selectively to the IBABP-L polynucleotide and performing a first amplification reaction to produce a first amplification product that indicates the presence of the IBABP-L polynucleotide in the sample; (b) contacting the sample with at least one primer that hybridizes selectively to IBABP polynucleotide and the IBABP-L polynucleotide and performing a second amplification reaction to produce a second amplification product that indicates the presence of IBABP polynucleotide and the IBABP-L polynucleotide in the sample; (c) measuring the first amplification product and the second amplification product; (d) calculating the ratio of IBABP-L polynucleotide to IBABP polynucleotide in the sample.

4. The method of claim 1 wherein the sample is selected from the group consisting of a cell, a tissue sample, a gastrointestinal tissue sample, a fecal sample, and a blood sample.

* * * * *

SEQUENCE LISTING

<160> NUMBER OF SEQ ID NOS: 16

<210> SEQ ID NO 1
<211> LENGTH: 1234
<212> TYPE: DNA
<213> ORGANISM: Homo sapiens

<400> SEQUENCE: 1

```
ggcgacaaca aaacagatta ctttgaaggg actagaagga ggacacaggg tcctggagga      60
aggcagctgg caagttacag agcagaaaga ctttgcacct ctggctccag ggagctcaca     120
ggcaggggct ggtccagccc agaggcgatg aagacagtga cgatgatgat ggtggtggag     180
atgcaggcgc tgactcagct gtctctctgt gactgtcttt gtgacagtct cattgttgtt     240
gttactaaga tggcttccct cagaggacgg acacttggag tagtggcagg ttcggccacc     300
cctagagacg atggcggtgg ggaccggggc agcccctgg ccccctgggc tcaccccct      360 cctgcgccac cccgggccgt gccgtgccaa gccggccacc agagggcgcg ccaggtcgcg     420
gcatcccggc tccccgtcgg cctggggccg gcgggcgggg ctcggctgtc tcctactgag     480
gcctcgcact tcctctcttg tacttctgtg tttcttggag agctgctcct tgaagatact     540
gctgcatgtg ggtctctgtg ggactgtcag ttaagagcct ccactggcct cacccacccc     600
cagagggaat acatgtcctc ggctgagccc attgggcttt ctctcctgac caatcagatt     660
```

```
atttctcttc tgactcaggt tctgagagct gtgttgtctg cgtgcacatg ggtgagccgg      720
aaaggagacc tgcagagaat gaaacagaca cataaaggaa agcctcccag cagcatggct      780
ttcaccggca agttcgagat ggagagtgag aagaattatg atgagttcat gaagctcctt      840
gggatctcca gcgatgtaat cgaaaaggcc cgcaacttca agatcgtcac ggaggtgcag      900
caggatgggc aggacttcac ttggtcccag cactactccg ggggccacac catgaccaac      960
aagttcactg ttggcaagga aagcaacata cagacaatgg ggggcaagac gttcaaggcc     1020
actgtgcaga tggagggcgg gaagctggtg gtgaatttcc ccaactatca ccagacctca     1080
gagatcgtgg gtgacaagct ggtggaggtc tccaccatcg gaggcgtgac ctatgagcgc     1140
gtgagcaaga gactggccta agcagccagg cccggcccag ggagctacaa acccaccaat     1200
aaaactgata taaggacaaa aaaaaaaaaa aaaa                                 1234

<210> SEQ ID NO 2
<211> LENGTH: 627
<212> TYPE: DNA
<213> ORGANISM: Homo sapiens

<400> SEQUENCE: 2
atgaagacag tgacgatgat gatggtggtg gagatgcagg cgctgactca gctgtctctc       60
tgtgactgtc tttgtgacag tctcattgtt gttgttacta agatggcttc cctcaggaga      120
cggacacttg gagtagtggc aggttcggcc acccctagag acgatggcgg tggggaccgg      180
ggcagccccc tggcccccctg gctcacccccc ctcctgcgc cacccccggg cgtgccgtgc      240
caagccggcc accagagggc gcgccaggtc gcggcatccc ggctccccgt cggcctgggg      300
ccggcgggcg gggctcggct gtctcctact gaggcctcgc acttcctctc ttgtacttct      360
gtgtttcttg gagagctgct ccttgaagat actgctgcat gtgggtctct gtgggactgt      420
cagttaagag cctccactgg cctcacccac cccagaggg aatacatgtc ctcggctgag      480
cccattgggc tttctctcct gaccaatcag attatttctc ttctgactca ggttctgaga      540
gctgtgttgt ctgcgtgcac atgggtgagc cggaaaggag acctgcagag aatgaaacag      600
acacataaag gaaagcctcc cagcagc                                          627

<210> SEQ ID NO 3
<211> LENGTH: 739
<212> TYPE: DNA
<213> ORGANISM: Homo sapiens

<400> SEQUENCE: 3
cagcgacaac aaaacagatt actttgaagg gactagaagg aggacacagg gtcctggagg       60
aaggcagctg gcaagttaca gagcagaaag actttgcacc tctggctcca gggagctcac      120
aggcaggggc tggtccagcc cagaggcgat gaagacagtg acgatgatga tggtggtgga      180
gatgcaggcg ctgactcagg ttctgagagc tgtgttgtct gcgtgcacat gggtgagccg      240
gaaaggagac ctgcagagaa tgaaacagac acataaagga aagcctccca gcagcatggc      300
tttcaccggc aagttcgaga tggagagtga agaattat gatgagttca tgaagctcct      360
tggggatctc cagcgatgta atcgaaaagg cccgcaactt caagatcgtc acggaggtgc      420
agcaggatgg gcaggacttc acttggtccc agcactactc cggggccac accatgacca      480 acaagttcac tgttggcaag gaaagcaaca tacagacaat ggggggcaag acgttcaagg      540
ccactgtgca gatggagggc gggaagctgg tggtgaattt ccccaactat caccagacct      600
cagagatcgt gggtgacaag ctggtggagg tctccaccat cggaggcgtg acctatgagc      660
```

```
gcgtgagcaa gagactggcc taagcagcca ggcccggccc agggagctac aaacccacca      720
ataaaactga tataaggac                                                   739

<210> SEQ ID NO 4
<211> LENGTH: 571
<212> TYPE: DNA
<213> ORGANISM: Homo sapiens

<400> SEQUENCE: 4
gaagaagtgg ggtgacttag gggctgagcc tcagcaactg ggagagttta taagctggat       60
agcagacccc tcagcaccac ccattctcct catccctctg ctctctggcc tccagcctcc      120
cagcagcatg gctttcaccg gcaagttcga gatggagagt gagaagaatt atgatgagtt      180
catgaagctc cttggggatc tccagcgatg taatcgaaaa ggcccgcaac ttcaagatcg      240
tcacggaggt gcagcaggat gggcaggact tcacttggtc ccagcactac tccgggggcc      300
acaccatgac caacaagttc actgttggca aggaaagcaa catacagaca atgggggca       360 agacgttcaa ggccactgtg cagatggagg gcgggaagct ggtggtgaat tcccccaact      420 atcaccgac ctcagagatc gtgggtgaca agctggtgga ggtctccacc atcggaggcg      480
tgacctatga gcgcgtgagc aagagactgg cctaagcagc caggcccggc ccagggagct      540
acaaacccac caataaaact gatataagga c                                     571

<210> SEQ ID NO 5
<211> LENGTH: 607
<212> TYPE: DNA
<213> ORGANISM: Homo sapiens

<400> SEQUENCE: 5
atgaagacag tgacgatgat gatggtggtg gagatgcagg cgctgactca ggttctgaga       60
gctgtgttgt ctgcgtgcac atgggtgagc cggaaaggag acctgcagag aatgaaacag      120
acacataaag gaaagcctcc cagcagcatg gctttcaccg gcaagttcga gatggagagt      180
gagaagaatt atgatgagtt catgaagctc cttgggatct ccagcgatgt aatcgaaaag      240
gcccgcaact tcaagatcgt cacggaggtg cagcaggatg ggcaggactt cacttggtcc      300
cagcactact ccgggggcca caccatgacc aacaagttca ctgttggcaa ggaaagcaac      360
atacagacaa tggggggcaa gacgttcaag gccactgtgc agatggaggg cgggaagctg      420
gtggtgaatt cccccaacta tcaccagacc tcagagatcg tgggtgacaa gctggtggag      480
gtctccacca tcggaggcgt gacctatgag cgcgtgagca agagactggc ctaagcagcc      540
aggcccggcc cagggagcta caaacccacc aataaaactg atataaggac aaaaaaaaaa      600
aaaaaaa                                                                607

<210> SEQ ID NO 6
<211> LENGTH: 147
<212> TYPE: DNA
<213> ORGANISM: Homo sapiens

<400> SEQUENCE: 6
atgaagacag tgacgatgat gatggtggtg gagatgcagg cgctgactca ggttctgaga       60
gctgtgttgt ctgcgtgcac atgggtgagc cggaaaggag acctgcagag aatgaaacag      120
acacataaag gaaagcctcc cagcagc                                          147

<210> SEQ ID NO 7
<211> LENGTH: 176
```

-continued

```
<212> TYPE: PRT
<213> ORGANISM: Homo sapiens

<400> SEQUENCE: 7

Met Lys Thr Val Met Met Val Val Glu Met Gln Ala Leu Thr Gln
1               5                   10                  15

Val Leu Arg Ala Val Leu Ser Ala Cys Thr Trp Val Ser Arg Lys Gly
            20                  25                  30

Asp Leu Gln Arg Met Lys Gln Thr His Lys Gly Lys Pro Pro Ser Ser
        35                  40                  45

Met Ala Phe Thr Gly Lys Phe Glu Met Glu Ser Glu Lys Asn Tyr Asp
    50                  55                  60

Glu Phe Met Lys Leu Leu Gly Ile Ser Ser Asp Val Ile Glu Lys Ala
65                  70                  75                  80

Arg Asn Phe Lys Ile Val Thr Glu Val Gln Gln Asp Gly Gln Asp Phe
                85                  90                  95

Thr Trp Ser Gln His Tyr Ser Gly Gly His Thr Met Thr Asn Lys Phe
            100                 105                 110

Thr Val Gly Lys Glu Ser Asn Ile Gln Thr Met Gly Gly Lys Thr Phe
        115                 120                 125

Lys Ala Thr Val Gln Met Glu Gly Gly Lys Leu Val Val Asn Phe Pro
    130                 135                 140

Asn Tyr His Gln Thr Ser Glu Ile Val Gly Asp Lys Leu Val Glu Val
145                 150                 155                 160

Ser Thr Ile Gly Gly Val Thr Tyr Glu Arg Val Ser Lys Arg Leu Ala
                165                 170                 175

<210> SEQ ID NO 8
<211> LENGTH: 128
<212> TYPE: PRT
<213> ORGANISM: Homo sapiens

<400> SEQUENCE: 8

Met Ala Phe Thr Gly Lys Phe Glu Met Glu Ser Glu Lys Asn Tyr Asp
1               5                   10                  15

Glu Phe Met Lys Leu Leu Gly Ile Ser Ser Asp Val Ile Glu Lys Ala
            20                  25                  30

Arg Asn Phe Lys Ile Val Thr Glu Val Gln Gln Asp Gly Gln Asp Phe
        35                  40                  45

Thr Trp Ser Gln His Tyr Ser Gly Gly His Thr Met Thr Asn Lys Phe
    50                  55                  60

Thr Val Gly Lys Glu Ser Asn Ile Gln Thr Met Gly Gly Lys Thr Phe
65                  70                  75                  80

Lys Ala Thr Val Gln Met Glu Gly Gly Lys Leu Val Val Asn Phe Pro
                85                  90                  95

Asn Tyr His Gln Thr Ser Glu Ile Val Gly Asp Lys Leu Val Glu Val
            100                 105                 110

Ser Thr Ile Gly Gly Val Thr Tyr Glu Arg Val Ser Lys Arg Leu Ala
        115                 120                 125

<210> SEQ ID NO 9
<211> LENGTH: 177
<212> TYPE: PRT
<213> ORGANISM: Homo sapiens

<400> SEQUENCE: 9

Met Lys Thr Val Thr Met Met Val Val Glu Met Gln Ala Leu Thr
1               5                   10                  15
```

```
Gln Val Leu Arg Ala Val Leu Ser Ala Cys Thr Trp Val Ser Arg Lys
             20                  25                  30
Gly Asp Leu Gln Arg Met Lys Gln Thr His Lys Gly Lys Pro Pro Ser
         35                  40                  45
Ser Met Ala Phe Thr Gly Lys Phe Glu Met Glu Ser Glu Lys Asn Tyr
     50                  55                  60
Asp Glu Phe Met Lys Leu Leu Gly Ile Ser Ser Asp Val Ile Glu Lys
 65                  70                  75                  80
Ala Arg Asn Phe Lys Ile Val Thr Glu Val Gln Gln Asp Gly Gln Asp
                 85                  90                  95
Phe Thr Trp Ser Gln His Tyr Ser Gly Gly His Thr Met Thr Asn Lys
            100                 105                 110
Phe Thr Val Gly Lys Glu Ser Asn Ile Gln Thr Met Gly Gly Lys Thr
        115                 120                 125
Phe Lys Ala Thr Val Gln Met Glu Gly Gly Lys Leu Val Val Asn Phe
    130                 135                 140
Pro Asn Tyr His Gln Thr Ser Glu Ile Val Gly Asp Lys Leu Val Glu
145                 150                 155                 160
Val Ser Thr Ile Gly Gly Val Thr Tyr Glu Arg Val Ser Lys Arg Leu
                165                 170                 175
Ala

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccacccattc tcctcatccc tctgctc                                       27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
accaagtgaa gtcctgccca tcctg                                         25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acatgggtga gccggaaagg agac                                          24

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 13
ccggagtagt gctgggacca agtgaagt                                          28

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caagactgga gacaaagtgg                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatctgcaga cagacactgg                                                   20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Thr Trp Val Ser Arg Lys Gly Asp Leu Gln Arg Met Lys Gln Thr
  1               5                  10                  15

His Lys Gly Lys Pro Pro Ser Ser
             20
```